United States Patent
Chen et al.

(10) Patent No.: US 11,039,735 B2
(45) Date of Patent: Jun. 22, 2021

(54) SURGICAL TISSUE PROTECTION SHEATH

(71) Applicant: SPIWay LLC, Corte Castillo, CA (US)

(72) Inventors: Eugene Chen, Carlsbad, CA (US); Richard C. Ewers, Carlsbad, CA (US); Cang Lam, Irvine, CA (US); Stephanie Frimond, Carlsbad, CA (US)

(73) Assignee: SPIWAY LLC, Carlsbad, CA (US)

( * ) Notice: Subject to any disclaimer, the term of this patent is extended or adjusted under 35 U.S.C. 154(b) by 0 days.

(21) Appl. No.: 16/427,151

(22) Filed: May 30, 2019

(65) Prior Publication Data

US 2019/0274525 A1 Sep. 12, 2019

Related U.S. Application Data

(63) Continuation of application No. 15/680,947, filed on Aug. 18, 2017, which is a continuation-in-part of (Continued)

(51) Int. Cl.
*A61B 1/32* (2006.01)
*A61B 1/00* (2006.01)
(Continued)

(52) U.S. Cl.
CPC .......... *A61B 1/00154* (2013.01); *A61B 1/233* (2013.01); *A61B 1/32* (2013.01); *A61B 17/00234* (2013.01); *A61B 17/24* (2013.01); *A61B 17/29* (2013.01); *A61B 90/00* (2016.02); *A61B 17/3415* (2013.01);
(Continued)

(58) Field of Classification Search
CPC .......... A61B 1/00147; A61B 1/00154; A61B 1/233; A61B 1/32; A61B 17/3423; A61F 2/82; A61F 2/90
See application file for complete search history.

(56) References Cited

U.S. PATENT DOCUMENTS

| 2,335,936 A | 12/1943 | Hanlon |
| 3,568,678 A | 3/1971 | Pourquier et al. |

(Continued)

FOREIGN PATENT DOCUMENTS

| CA | 2185070 | 3/1997 |
| DE | 1057738 B | 5/1959 |

(Continued)

OTHER PUBLICATIONS

International Search Report and Written Opinion for International Application No. PCT/US2017/047550; dated Nov. 30, 2017; 16 pages.

*Primary Examiner* — Eduardo C Robert
*Assistant Examiner* — Steven J Cotroneo
(74) *Attorney, Agent, or Firm* — Perkins Coie LLP; Kenneth H. Ohriner

(57) ABSTRACT

A surgical sheath for use in endoscopic trans-nasal or intra-ocular surgery is made of a braid material. The sheath may be manufactured by placing a length of braided tube material over a mandrel. The braid material is conformed to the shape of the mandrel and is then heat set. An atraumatic end may be made by folding or rolling one or both ends of the sheath. A coating may also optionally be applied to the braid material. The sheath reduces collateral trauma to the tissues in the surgical pathway.

20 Claims, 20 Drawing Sheets

Related U.S. Application Data application No. 15/340,718, filed on Nov. 1, 2016, now Pat. No. 9,949,621, which is a continuation of application No. 14/626,184, filed on Feb. 19, 2015, now abandoned, which is a continuation of application No. 13/798,990, filed on Mar. 13, 2013, now Pat. No. 8,986,201.

(60) Provisional application No. 62/396,746, filed on Sep. 19, 2016, provisional application No. 62/377,400, filed on Aug. 19, 2016.

(51) Int. Cl.
　　*A61B 17/00* (2006.01)
　　*A61B 17/29* (2006.01)
　　*A61B 90/00* (2016.01)
　　*A61B 1/233* (2006.01)
　　*A61B 17/24* (2006.01)
　　*A61M 1/00* (2006.01)
　　*A61B 17/34* (2006.01)
　　*A61B 90/30* (2016.01)

(52) U.S. Cl.
　　CPC ....... *A61B 17/3423* (2013.01); *A61B 17/3431* (2013.01); *A61B 90/39* (2016.02); *A61B 2017/00278* (2013.01); *A61B 2017/00849* (2013.01); *A61B 2017/00876* (2013.01); *A61B 2017/2926* (2013.01); *A61B 2017/345* (2013.01); *A61B 2090/08021* (2016.02); *A61B 2090/306* (2016.02); *A61B 2217/005* (2013.01); *A61B 2217/007* (2013.01); *A61M 1/0084* (2013.01)

(56) References Cited

U.S. PATENT DOCUMENTS

| | | | |
|---|---|---|---|
| 3,664,330 A | | 5/1972 | Deutsch |
| 3,867,946 A | | 2/1975 | Huddy |
| 4,280,493 A | | 7/1981 | Council |
| 4,312,353 A | | 1/1982 | Shahbabian |
| 4,755,174 A | | 7/1988 | Milewski et al. |
| 4,819,619 A | | 4/1989 | Augustine et al. |
| 4,821,715 A | | 4/1989 | Downing |
| 4,883,465 A | | 11/1989 | Brennan |
| 5,011,474 A | | 4/1991 | Brennan |
| 5,139,510 A | | 8/1992 | Goldsmith, III et al. |
| 5,336,163 A | | 8/1994 | DeMane et al. |
| 5,400,770 A | | 3/1995 | Nakao et al. |
| 5,591,226 A | * | 1/1997 | Trerotola ............... A61B 17/11 |
| | | | 606/108 |
| 5,599,284 A | | 2/1997 | Shea |
| 5,601,591 A | | 2/1997 | Edwards et al. |
| 5,601,594 A | | 2/1997 | Best |
| 5,609,627 A | * | 3/1997 | Goicoechea ............ A61F 2/82 |
| | | | 128/898 |
| 5,709,713 A | * | 1/1998 | Evans .................... A61F 2/07 |
| | | | 606/191 |
| 5,713,839 A | | 2/1998 | Shea |
| 5,800,394 A | | 9/1998 | Yoon et al. |
| 5,827,224 A | | 10/1998 | Shippert |
| 5,846,261 A | * | 12/1998 | Kotula .................... A61F 2/01 |
| | | | 606/213 |
| 5,865,728 A | | 2/1999 | Moll et al. |
| 5,876,445 A | * | 3/1999 | Andersen ............... A61F 2/958 |
| | | | 623/23.7 |
| 5,925,074 A | * | 7/1999 | Gingras .................. A61F 2/07 |
| | | | 606/191 |
| 5,967,970 A | | 10/1999 | Cowan et al. |
| 5,993,407 A | | 11/1999 | Moazed |
| 6,033,426 A | | 3/2000 | Kaji |
| 6,083,155 A | | 7/2000 | Trese |
| 6,102,928 A | | 8/2000 | Bonutti |
| 6,183,493 B1 | | 2/2001 | Zammit |
| 6,186,965 B1 | | 2/2001 | Patterson |
| 6,245,099 B1 | * | 6/2001 | Edwin ................... A61F 2/07 |
| | | | 606/198 |
| 6,306,084 B1 | | 10/2001 | Pinczower |
| 6,309,345 B1 | | 10/2001 | Stelzer et al. |
| 6,328,753 B1 | | 12/2001 | Zammit |
| 6,386,197 B1 | | 5/2002 | Miller |
| 6,454,783 B1 | | 9/2002 | Piskun |
| 6,468,301 B1 | * | 10/2002 | Amplatz ................ A61F 2/856 |
| | | | 623/1.13 |
| 6,491,720 B1 | * | 12/2002 | Vallana .................. A61F 2/82 |
| | | | 623/1.42 |
| 6,607,546 B1 | | 8/2003 | Murken |
| 7,100,612 B2 | | 9/2006 | Dunlap |
| 7,361,168 B2 | | 4/2008 | Makower et al. |
| 7,410,480 B2 | | 8/2008 | Muni et al. |
| 7,520,876 B2 | | 4/2009 | Ressemann et al. |
| 7,654,997 B2 | | 2/2010 | Makower et al. |
| 7,678,099 B2 | | 3/2010 | Ressemann et al. |
| 7,720,521 B2 | | 5/2010 | Chang et al. |
| 7,727,186 B2 | | 6/2010 | Makower et al. |
| 7,730,888 B2 | | 6/2010 | Dunlap |
| 7,740,642 B2 | | 6/2010 | Becker |
| 7,753,929 B2 | | 7/2010 | Becker |
| 7,753,930 B2 | | 7/2010 | Becker |
| 7,771,409 B2 | | 8/2010 | Chang et al. |
| 7,799,337 B2 | | 9/2010 | Levin |
| 7,918,871 B2 | | 4/2011 | Truitt et al. |
| 7,976,488 B2 | * | 7/2011 | Levine .................. A61F 5/0076 |
| | | | 604/8 |
| 8,409,083 B2 | | 4/2013 | Mangiardi |
| 8,839,790 B2 | | 9/2014 | Beck Arnon |
| 8,986,201 B2 | | 3/2015 | Chen et al. |
| 9,011,326 B2 | | 4/2015 | Hannaford et al. |
| 9,610,181 B2 | * | 4/2017 | Zaver .................... A61F 2/01 |
| 10,406,005 B2 | * | 9/2019 | Han ...................... A61L 31/10 |
| 10,675,114 B2 | | 6/2020 | Ewers et al. |
| 2001/0016726 A1 | * | 8/2001 | Dubrul .................. A61M 25/10 |
| | | | 604/509 |
| 2001/0049554 A1 | * | 12/2001 | Ruiz ...................... A61F 2/06 |
| | | | 623/1.44 |
| 2002/0013511 A1 | | 1/2002 | Ailinger et al. |
| 2003/0014076 A1 | | 1/2003 | Mollenauer et al. |
| 2003/0154986 A1 | | 8/2003 | Fariss et al. |
| 2003/0216770 A1 | | 11/2003 | Persidsky et al. |
| 2004/0116999 A1 | * | 6/2004 | Ledergerber ........... A61F 2/07 |
| | | | 623/1.14 |
| 2004/0138525 A1 | | 7/2004 | Saadat et al. |
| 2004/0210114 A1 | | 10/2004 | Simon |
| 2004/0230100 A1 | | 11/2004 | Shluzas |
| 2004/0243172 A1 | | 12/2004 | Hogle |
| 2005/0059960 A1 | | 3/2005 | Simaan et al. |
| 2005/0075540 A1 | | 4/2005 | Shluzas et al. |
| 2005/0090717 A1 | * | 4/2005 | Bonadio ................ A61B 1/32 |
| | | | 600/208 |
| 2005/0165366 A1 | | 7/2005 | Brustad et al. |
| 2005/0192482 A1 | * | 9/2005 | Carpenter .......... A61B 1/00142 |
| | | | 600/203 |
| 2005/0192608 A1 | | 9/2005 | Moreno et al. |
| 2005/0240147 A1 | | 10/2005 | Makower et al. |
| 2006/0004323 A1 | | 1/2006 | Chang et al. |
| 2006/0041270 A1 | | 2/2006 | Lenker et al. |
| 2006/0095050 A1 | | 5/2006 | Hartley et al. |
| 2006/0173407 A1 | | 8/2006 | Shaughnessy et al. |
| 2006/0190075 A1 | * | 8/2006 | Jordan ................... A61F 2/90 |
| | | | 623/1.23 |
| 2006/0200003 A1 | | 9/2006 | Youssef |
| 2006/0212062 A1 | | 9/2006 | Farascioni |
| 2006/0287583 A1 | | 12/2006 | Mangiardi |
| 2007/0005094 A1 | | 1/2007 | Eaton et al. |
| 2007/0016174 A1 | | 1/2007 | Millman et al. |
| 2007/0021773 A1 | | 1/2007 | Nolte |
| 2007/0055107 A1 | | 3/2007 | Wenchell |
| 2007/0100370 A1 | | 5/2007 | Hogle |
| 2007/0191876 A1 | * | 8/2007 | Dubrul .................. A61F 5/56 |
| | | | 606/199 |
| 2007/0203474 A1 | | 8/2007 | Ryan et al. |

(56) References Cited

U.S. PATENT DOCUMENTS

| | | |
|---|---|---|
| 2007/0219575 A1 | 9/2007 | Mejia |
| 2007/0225568 A1 | 9/2007 | Colleran |
| 2007/0277831 A1 | 12/2007 | Luhrs |
| 2007/0293726 A1 | 12/2007 | Goldfarb et al. |
| 2007/0299314 A1 | 12/2007 | Bertolero et al. |
| 2008/0027464 A1 | 1/2008 | Moll et al. |
| 2008/0045803 A1 | 2/2008 | Williams et al. |
| 2008/0058590 A1 | 3/2008 | Saadat et al. |
| 2008/0065105 A1 | 3/2008 | Larkin et al. |
| 2008/0065108 A1 | 3/2008 | Diolaiti |
| 2008/0071288 A1 | 3/2008 | Larkin et al. |
| 2008/0097514 A1 | 4/2008 | Chang et al. |
| 2008/0097516 A1 | 4/2008 | Chang et al. |
| 2008/0109026 A1 | 5/2008 | Kassam |
| 2008/0132938 A1 | 6/2008 | Chang et al. |
| 2008/0188868 A1 | 8/2008 | Weitzner et al. |
| 2008/0234550 A1 | 9/2008 | Hawkes et al. |
| 2008/0243064 A1 | 10/2008 | Stahler et al. |
| 2008/0255519 A1 | 10/2008 | Piskun et al. |
| 2008/0275483 A1 | 11/2008 | Makower et al. |
| 2009/0010991 A1 | 1/2009 | Prabhu et al. |
| 2009/0054728 A1 | 2/2009 | Trusty |
| 2009/0062927 A1 | 3/2009 | Marten et al. |
| 2009/0082840 A1* | 3/2009 | Rusk ................. A61F 2/95 623/1.11 |
| 2009/0137952 A1 | 5/2009 | Ramamurthy et al. |
| 2009/0250067 A1* | 10/2009 | Beck Arnon ........ A61M 15/08 128/207.18 |
| 2009/0312745 A1 | 12/2009 | Goldfarb et al. |
| 2010/0030031 A1 | 2/2010 | Goldfarb et al. |
| 2010/0076555 A1 | 3/2010 | Marten et al. |
| 2010/0100181 A1 | 4/2010 | Makower et al. |
| 2010/0145147 A1 | 6/2010 | Pinsky et al. |
| 2010/0174149 A1 | 7/2010 | Moll et al. |
| 2010/0174308 A1 | 7/2010 | Chang et al. |
| 2010/0179537 A1 | 7/2010 | Rashidi |
| 2010/0211181 A1 | 8/2010 | Prabhu et al. |
| 2010/0228227 A1 | 9/2010 | Krespi et al. |
| 2010/0249523 A1 | 9/2010 | Spiegel et al. |
| 2010/0298862 A1 | 11/2010 | Chang et al. |
| 2010/0331777 A1 | 12/2010 | Danielsson |
| 2011/0004194 A1 | 1/2011 | Eaton et al. |
| 2011/0005529 A1 | 1/2011 | Doshi et al. |
| 2011/0048430 A1* | 3/2011 | Arnon ................. A61F 5/08 128/848 |
| 2011/0118551 A1* | 5/2011 | Ciporen ............. A61B 17/3423 600/201 |
| 2011/0125092 A1 | 5/2011 | Hepworth et al. |
| 2012/0203069 A1 | 8/2012 | Hannaford et al. |
| 2013/0092173 A1* | 4/2013 | Alexander ........... A61B 1/0638 128/207.18 |
| 2013/0190571 A1* | 7/2013 | Chen ................. A61B 17/24 600/204 |
| 2013/0190572 A1 | 7/2013 | Chen et al. |
| 2014/0024994 A1* | 1/2014 | Khoury .................. A61F 2/064 604/9 |
| 2015/0209074 A1* | 7/2015 | Payne ................ A61B 17/3423 600/114 |
| 2016/0249934 A1 | 9/2016 | Hewitt et al. |
| 2017/0347865 A1 | 12/2017 | Chen et al. |
| 2018/0303631 A1 | 10/2018 | Phan et al. |
| 2018/0361129 A1* | 12/2018 | Renner ................. A61M 29/02 |
| 2019/0000667 A1* | 1/2019 | Dollberg ............. A61B 18/06 |

FOREIGN PATENT DOCUMENTS

| | | |
|---|---|---|
| DE | 202012100028 U1 | 4/2012 |
| DE | 102010054786 A1 | 6/2012 |
| DE | 202010017673 U1 | 10/2012 |
| EM | 002429829-001 | 3/2014 |
| EP | 178165 A1 | 5/2007 |
| FR | 2260979 A1 | 9/1975 |
| FR | 2825281 A1 | 12/2002 |
| FR | 2985660 A1 | 7/2013 |
| JE | 1222209 B | 8/1966 |
| WO | 2010107894 A1 | 9/2010 |
| WO | 2011013122 A2 | 2/2011 |
| WO | 2011013122 A3 | 4/2011 |
| WO | 2015198032 A1 | 12/2015 |

\* cited by examiner

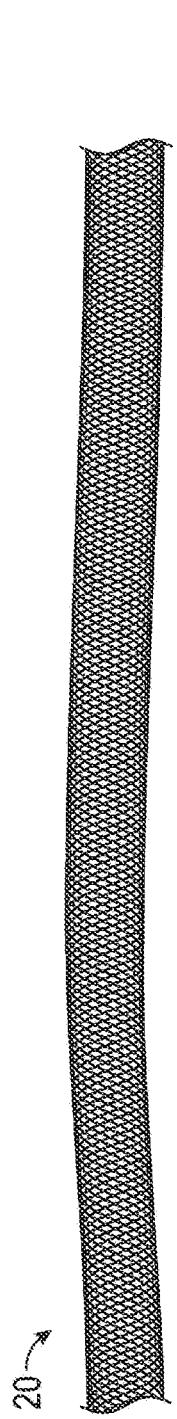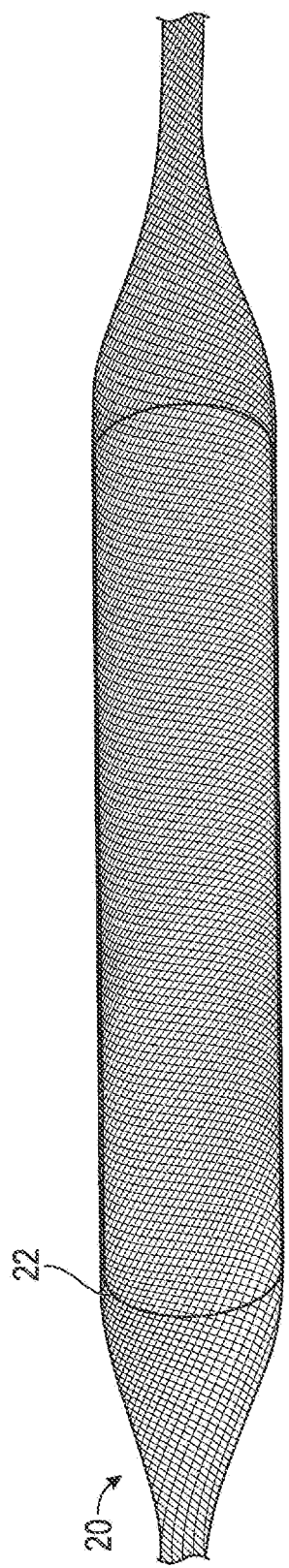

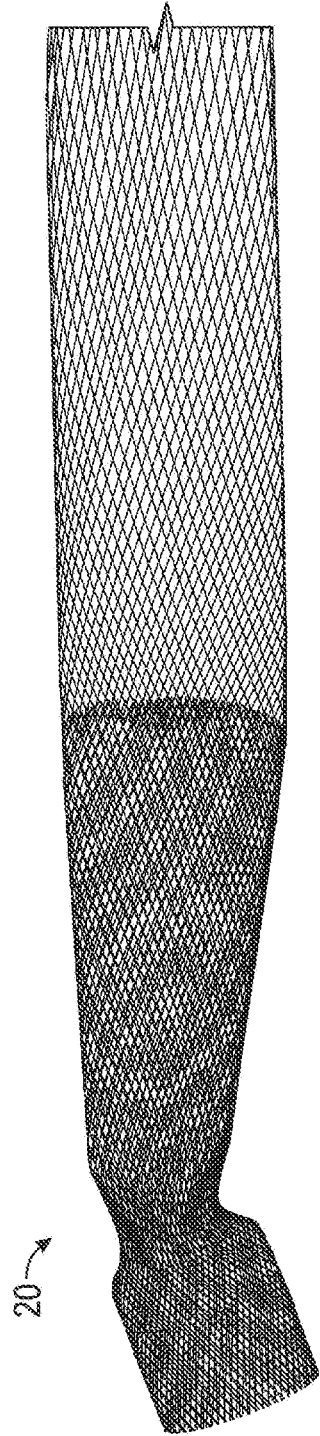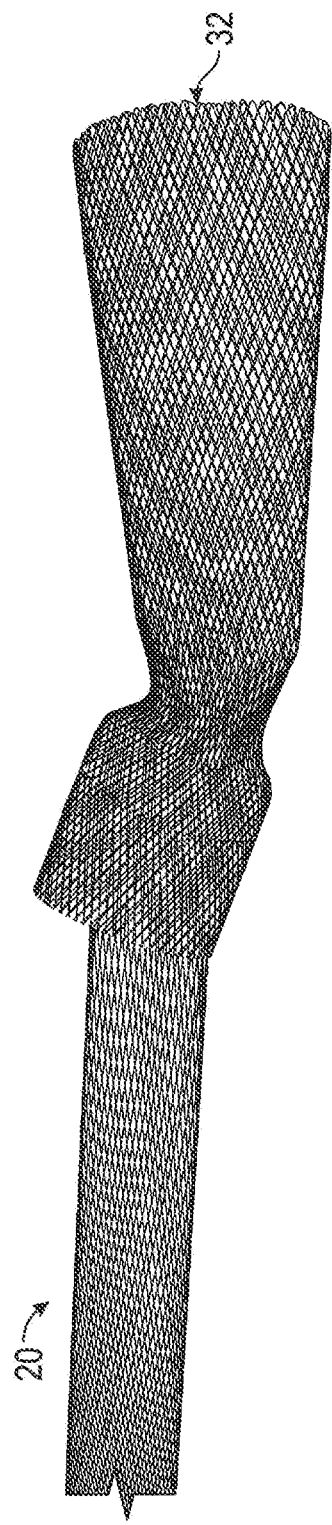
FIG. 7A
FIG. 7B

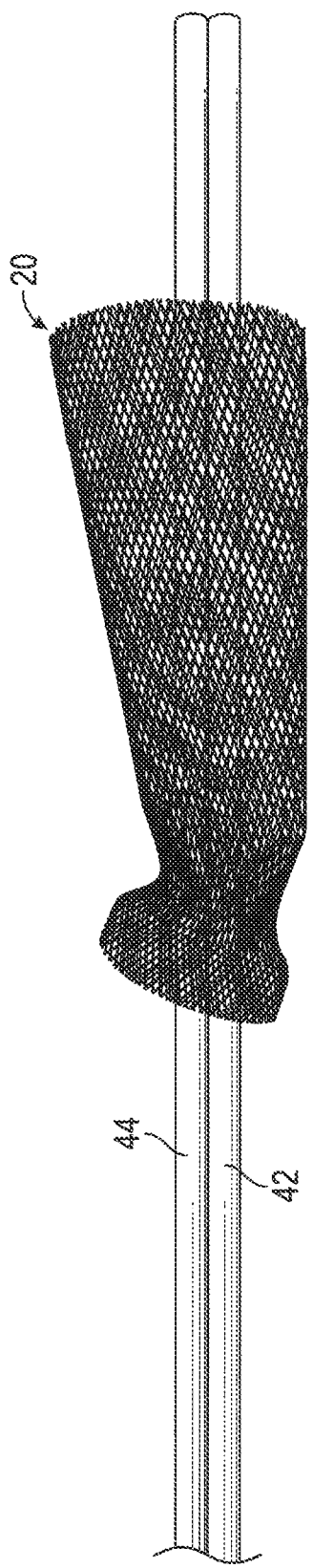
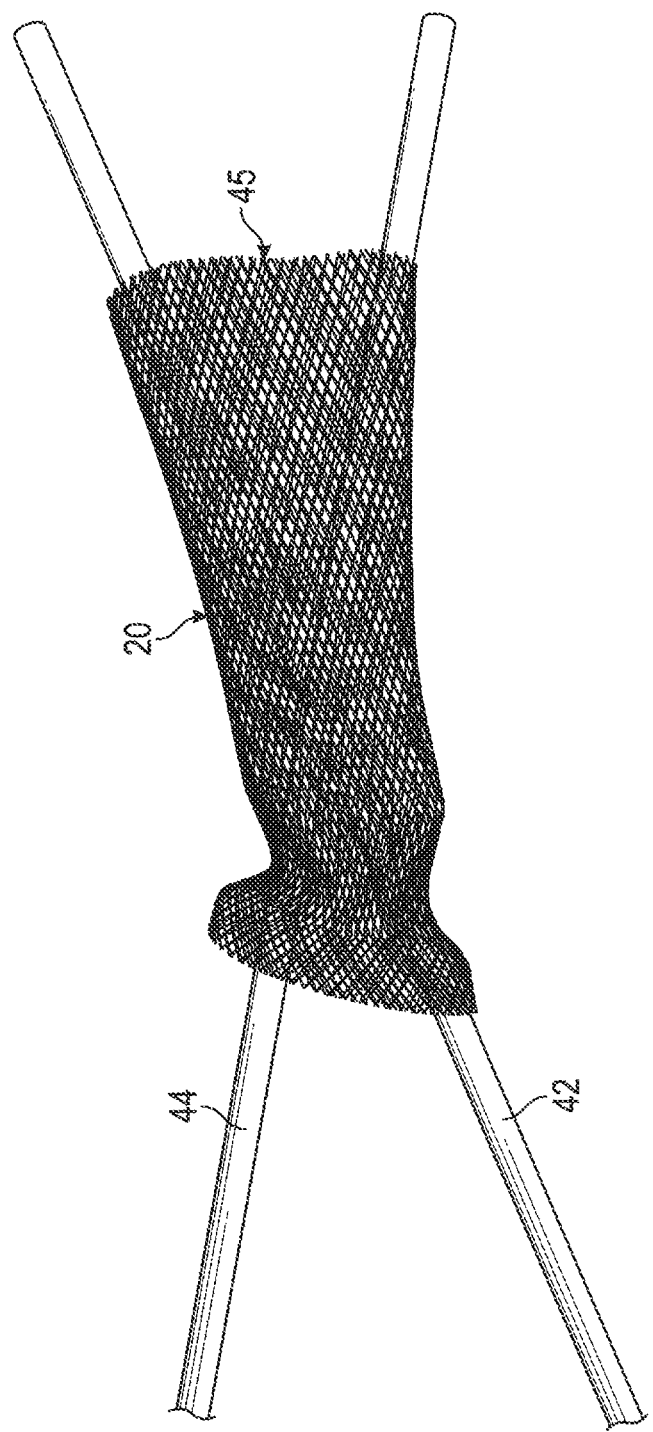

SURGICAL TISSUE PROTECTION SHEATH

This application is a continuation of U.S. patent application Ser. No. 15/680,947, filed Aug. 18, 2017 and now abandoned, which application claims the benefit of and priority to U.S. Provisional Patent Application No. 62/396,746 filed Sep. 19, 2016 and U.S. Provisional Patent Application No. 62/377,400 filed Aug. 19, 2016, and which is a continuation-in-part of U.S. patent application Ser. No. 15/340,718 filed Nov. 1, 2016, now U.S. Pat. No. 9,949,621, which is a continuation of U.S. patent application Ser. No. 14/626,184 filed Feb. 19, 2015, which is a continuation of U.S. patent application Ser. No. 13/798,990 filed Mar. 13, 2013, now U.S. Pat. No. 8,986,201. Each of the applications listed above are incorporated herein in their entireties by reference.

BACKGROUND

Endoscopic surgery within the head is a common procedure in neurological surgery and otolaryngology. It avoids large cranial incisions and can reduce the need brain retraction and prolonged wound healing. Endoscopic surgery within the head also provides improved illumination and visualization of the target tissues because the camera of the endoscope is brought directly to the surgical site.

During this type of surgery, there may be local trauma to the tissues in the surgical pathway, resulting from pressure or abrasion caused by the surgical tools. Generally these tissues are the nasal mucosa, turbinates, nasal septum, and sphenoid/frontal/maxillary sinus. When transorbital approaches are used, orbital and periorbital tissue are subject to local trauma. Surgical pathway trauma can add to the trauma of the procedure and prolong the patient's recovery time. Liquids in the surgical pathway, such as mucous, blood, and soiled irrigation fluid, tend to obscure the view of the endoscope. This leads to the constant need for irrigation and suction of the obstructing liquids. In some cases the endoscope may also have to be removed, cleaned and replaced multiple times during a single procedure. This disadvantage tends to increase the complexity and time requirements of the operation. In addition, with each movement of a surgical tool into or out of the surgical pathway, the surrounding tissues are put at risk of additional trauma. Improved devices and methods are therefore needed.

SUMMARY OF THE INVENTION

An access sheath is provided to protect the nasal passageway during endoscopic trans nasal or intra ocular surgery. The access sheath protects the entrance of the nares and sinus from the placement and manipulation of surgical tools both during the initial placement and during manipulation and exchange of surgical tools. The access sheath may provide a guide port to help direct surgical tools into position. In some designs the access sheath may splint the sinus open, to help open and provide access past the turbinate. The access sheath may also help to keep surgical tools and especially an endoscope freer from obscuring matter and secretions The access sheath may be flexible for placement in a folded or rolled up configuration, have a hoop or expansion capability to fill and splint the passage, be partially or totally fluid tight to reduce ingress of secretions, and be lubricious for the unobstructed motion of fine surgical tools during delicate micro surgery.

U.S. Pat. No. 8,986,201 B2 discloses an access sheath, which may be made of elastomer, and has many of the performance features described above. However, elastomer has an inherent draw back. Flexible elastomers are inherently tacky and hence create sliding friction on surgical tools. In some designs this has required additives or a coating on the surface of access sheath to reduce friction. Still generally additives and coatings cannot always provide the surgeon with the feel of a surgical tool sliding against a wet mucus layer.

A nasal access sheath made of a hard plastic material is manufactured in a way to make it flexible, in one embodiment, by using a braided tube. A braid can be made from multiple fibers of plastic monofilament. Monofilaments can be made of rigid and tough plastic such as PET (Polyethylene terephthalate) or Nylon. Monofilaments can even be made from stainless steel. The fibers remain flexible because they have a small diameter, such as 0.08 mm to 0.5 mm. The fibers may have a round cross section, a relatively flat cross section, or elliptical cross section, A plurality of fibers can be braided into a braided tube. As one example, 64 fibers are counter wound in a two over and two under braid. The angle (pics or pitch) of the braided fibers can select the circular profile of the resulting braided tube or sleeve. A braided tube additionally is flexible due to the loose association of the braided fibers and their ability to slide relative to each other but still maintain the intended braided pattern.

BRIEF DESCRIPTION OF THE DRAWINGS

In the drawings, the same reference number indicates the same element in each of the views.

FIG. 1 shows a braided tube.

FIG. 2 shows a braided tube expanded and loaded over a cylindrical mandrel.

FIG. 7A shows a braided tube created by a single layer of braid formed with a continuation distally of unformed braid. The formed portion was then dipped in a coating of elastomer.

FIG. 7B show the structure of 7A, where the uncoated distal extension of braid has been inverted back through the formed and coated section.

FIG. 9A shows the coated braided tube of FIG. 7C or 8B with two surgical tools placed in parallel.

FIG. 9B shows the coated braided tube with two surgical tools at an acute angle and the flexible response of the neck of the structure.

DETAILED DESCRIPTION

FIG. 1 shows a braided tube 20 in its natural braided state. In FIG. 2 the braid is shown on a cylindrical mandrel 22 to demonstrate its tubular shape and ability to expand. The braided tube 20 can be drawn down to a smaller diameter by stretching and pulling the monofilaments into a more longitudinal alignment. Conversely, the braided tube 20 can be expanded to a larger diameter by compression and pushing the filaments into a more radial directed alignment.

The braided tube 20, especially if made of plastic, can be placed around a mandrel 22 that causes the braided tube 20 to expand to a specific diameter or shape. The braided tube 20 can then be heat set in an oven. Upon cooling the braided tube 20 will be permanently formed into the shape of the mandrel 22. Heat setting mandrels can be made of hollow or solid stainless steel, Delrin (acetal homopolymer resin). Mandrels 22 may be made of Teflon (fluoropolymer), especially if intended to coat the braided tube in a plastic/rubber/silicone dispersion. Heat setting can be done at a variety of temperatures and time, depending on the braided tube material and the heat capacity of the mandrel 22. A useful heat set temperature for nylon or PET braids is 120° C. and 150° C. for half an hour, followed by cooling to room temperature in ambient conditions or a quench in water.

FIG. 2 shows braided tube 20 loaded over a Delrin® forming mandrel 22 prior to heat setting. The mandrel 22 may be sized and shaped to product an access sheath having the shape and dimensions discussed in U.S. Pat. No. 8,986,201, incorporated herein by reference, and as shown in FIGS. 15-22.

Figure 3A:
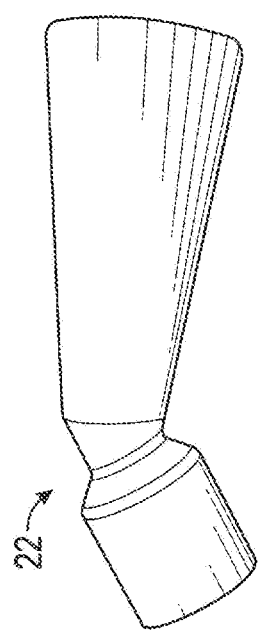
FIG. 3A shows a forming mandrel shaped with a preferred geometry for use in the human sinus.
Figure 3B:
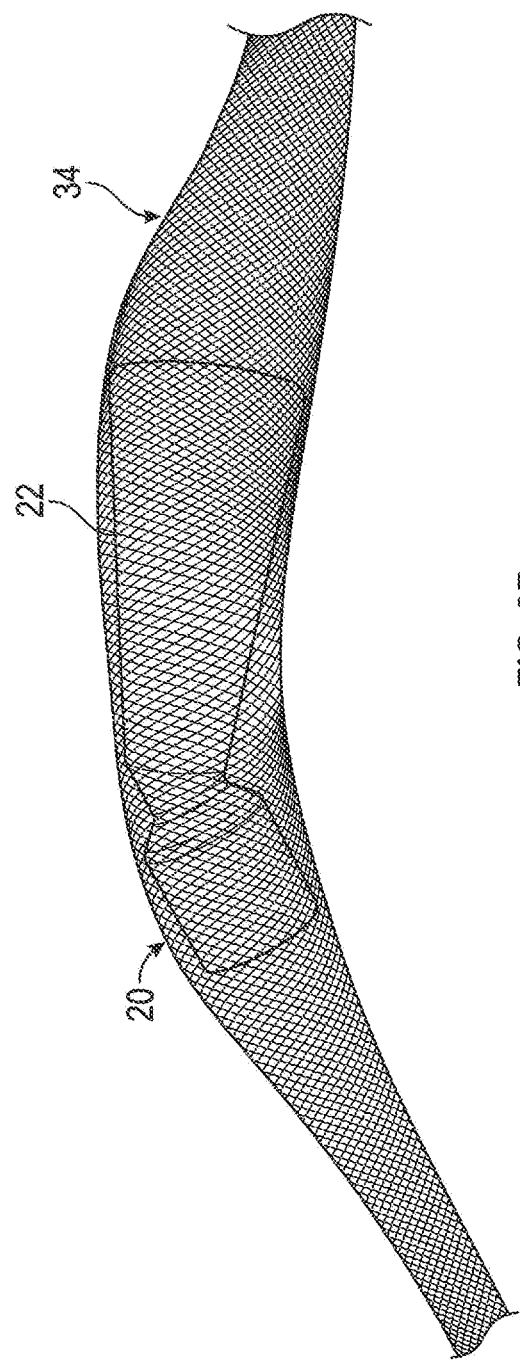
FIG. 3B shows a braided tube expanded and loaded over the forming mandrel of FIG. 3A.

FIG. 3A shows a forming mandrel 22 in a preferred geometry for manufacturing an access sheath 40. FIG. 3B shows a braided tube 20 placed over and around the mandrel 22. After the braided tube 20 is loaded over the forming mandrel 22, the braided tube 20 may be conformed to the shape of the mandrel 22 by a partial or complete wrapping of self-adhering silicone tape over the braided tube 20, or alternatively via a shaping block pressed onto the braided tube 20 on the mandrel 22, with the shaping block having an internal opening complimentary to the mandrel, but sized to account for the thickness of the braided tube 20.

Figure 4:
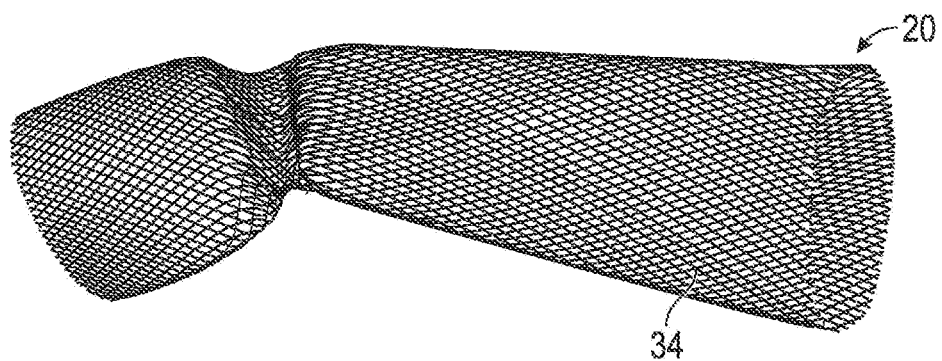
FIG. 4 shows a braided tube that has been heat formed and the mandrel of FIG. 3A removed.

FIG. 4 shows the braided tube 20 after it has been heat formed, removed from the mandrel 22 and trimmed at both distal and proximal ends. This results in a highly flexible, thin, and simple to manufacture access sheath 40. This sheath 40 is permeable which allows natural mucus lubrication of the sinus to enter into the access sheath for additional lubricity. The braiding pattern may be modified to allow more or less permeability by changing the diameter of fibers or filaments of the braid material. Flat monofilament or multi-filar fibers may be used to increase the PIC (how tight the braiding is formed), and reduce the interstitial spacing between fibers of the braided tube 20.

The braided tube 20 may be coated with a semipermeable or more preferably an impermeable membrane. A less tacky coating or a harder urethane material, of durometer 50 A or harder, may be used. It can be applied in thicknesses of 0.1 mm to 0.3 mm. Due to the thinness and the flexibility of the braided tube, even when coated the braided tube may still remain flexible, foldable, and be able to elongate.

In an alternate embodiment a PET (Polyethylene Terephthalate) braided tube can be used with a uniform coat of a silicone dispersion (Nusil MED16-6606). Despite being silicone this combination provides a slick surface relative to surgical tools. This can be attributed to the mechanical nature of the structure. The braid surface provides a non-continuous, undulating surface where a full surface contact is replaced by a series of discrete contact points. Discrete contact points reduce the surface area of contact and hence reduce the friction between access sheath 40 and the surgical tool.

A single layer braided tube coated in an impermeable silicone, such as NUSIL silicone dispersion 6061, was found to be a good coating as it applies in a thin layer and despite being silicone (that has inherent tackiness) has little tack. The resulting friction as tested showed 50 grams of friction.

This is about the same friction as hydrophilic coated devices when tested new. The lubricious nature of the material also does not degrade over time, unlike hydrophilic coatings.

Examples of lubricious coatings are: ceramic coatings. Slick-Sil coating (by Surface Solutions Group), Parylene coating, and hydrophilic coatings. Similar coatings can provide better friction reduction but may not feel as lubricious as mucous membrane.

Hydrophilic coating provide lubricity similar to mucous membranes, however they require wetting with water or saline to activate, and need periodic or continuous re-wetting to stay slick. Hydrophilic coatings also wear away after multiple abrasions with surgical tools and may not withstand the long procedure time of skull base neurosurgery. Examples of lubricious additives are: barium sulfate, powdered Teflon (fluoropolymer) glass fillers, and ceramic fillers. These can reduce the surface tack but also tend to provide a surgical tool feel that is different from mucous membranes.

The elastomeric coating on the internal surface of the braided tube 20 may be reduced. If the mandrel 22 is created from a semi flexible rubber or jacketed in rubber it results in a flexible surface. If the braided tube 20 is loaded over this surface and stretched to tightly engage the mandrel 22, the internal contact points of the braided tube embed slightly into the semi-flexible mandrel surface. This effectively masks the internal surface of the braid. A coating step fully coats the external braided tube while leaving the highest contact points of the internal braided tube uncoated and fully retaining the inherent lubricity of the hard plastic monofilament of the braided tube. A semi flexible surface may also be achieved by jacketing the mandrel in polyolefin shrink tubing. When the braid/jacket mandrel are heated for shaping, the shrink tubing softens and the braided tube will slightly embed. This similarly creates a braid/mandrel assembly that has a partially masked inner braid surface for a follow up coating step.

Figure 5:
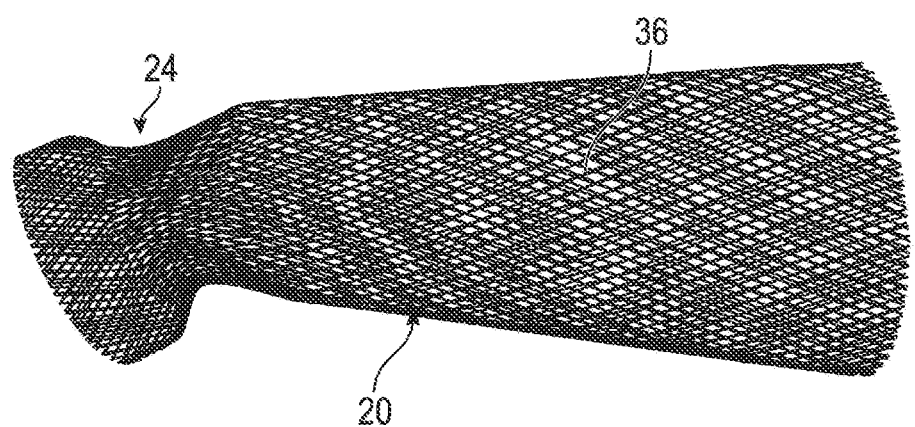
FIG. 5 shows a heat formed braided tube that has been coated with an elastomer.

FIG. 5 shows a formed braided tube that has been coated in the silicone dispersion described above. The distal end may be made atraumatic for insertion in the delicate anatomy of the nasal cavity, for example by using a double layer 36 of the braided tube material, in contrast to the single layer 34 shown in FIG. 4. The double layer 36 may be provided by inverting the braided tube 20 to create a dual wall braided tube with an un-cut, rolled or rounded edge 32.

Figure 6:
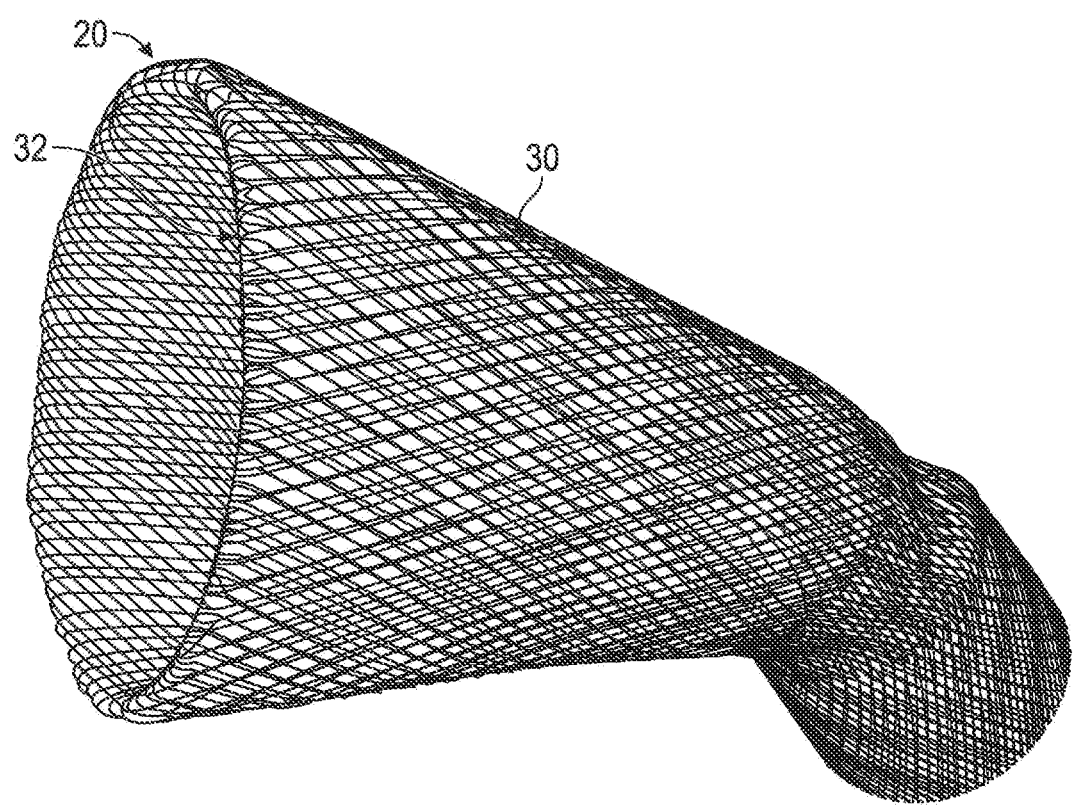
FIG. 6 shows a heat formed braided tube with the braid inverted to form a dual layer, and with the distal end folded back on itself to provide a rounded tip.

FIG. 6 shows a formed braided tube 20 having an inverted braid section 30 to create the rounded edge 32. The rounded edge 32 can be dipped completely into a coating. This creates an impermeable surface in a simple way, although it may reduce flexibility or the ability to draw down and fold since both braid layers are bonded together.

Figure 7C:
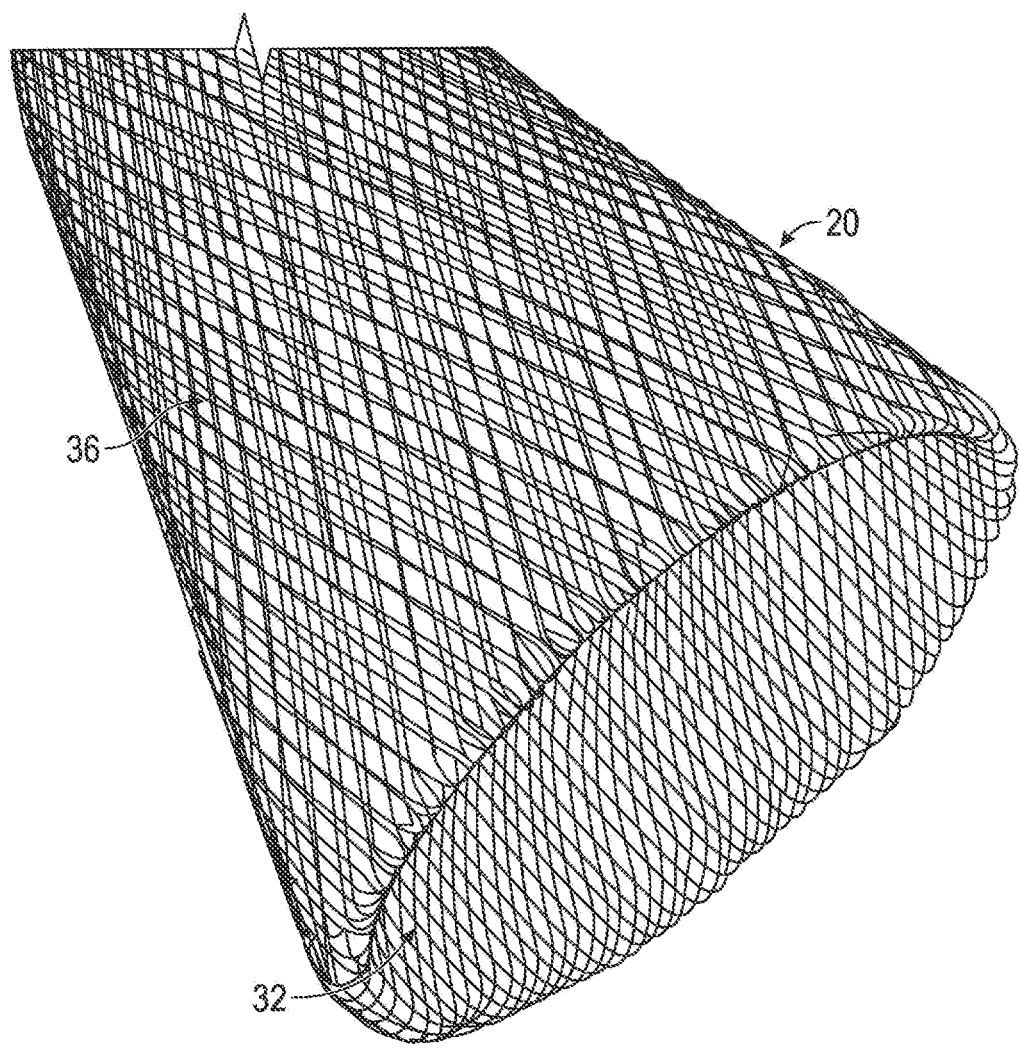
FIG. 7C shows the structure of FIG. 7A where the uncoated distal extension of braid was then inverted resulting in a braided tube having a rounded distal end and an un-coated inner surface and a coated outer section.

FIGS. 7A-7C show an alternative to the rounded edge design of FIG. 6, with the benefit of the rounded edge 32 has no coating on the inner surface, while the outer surface is coated, and does not bond the layers together preserving a thinner wall and flexibility.

Figure 8B:
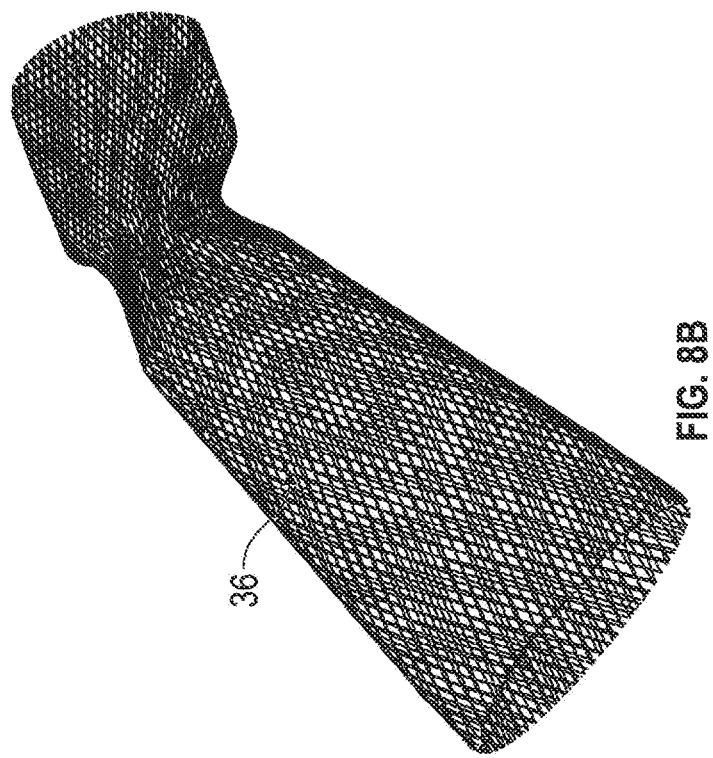
FIG. 8B shows the distal end of a two layer braided tube with an inverted distal end.
Figure 8A:
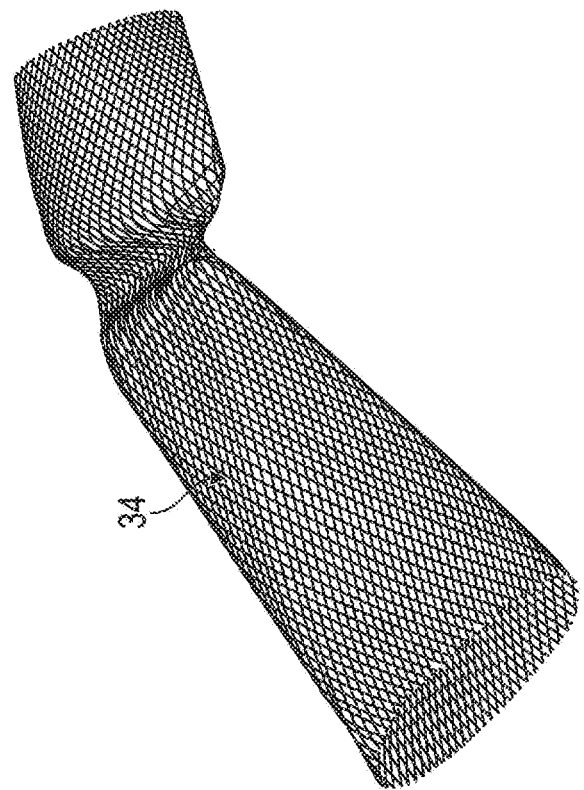
FIG. 8A shows the distal end or edge of a single layer braided tube.

Referring now to FIG. 7A, the right side of the braided tube 20 is formed on a mandrel 22 and then coated. The left side is not formed or coated. Referring now to FIG. 7B, the uncoated braid (left side) is inverted and loaded through the shaped and coated right side portion. Referring now to FIG. 7C, the rounded edge 32 (formed via the inverting step) and the coated external surface and uncoated internal surface are shown. For comparison, FIG. 8A shows an access sheath with a straight edge while FIG. 8B shows an access sheath 40 with a rounded edge 32.

As is apparent from the description of FIGS. 3-8B above, a method of making a surgical access sheath may include placing a length of braided tube material over a mandrel; conforming the braided tube material to the shape of the mandrel; heating the braided tube material to heat set the braided tube material; removing the braided tube material from the mandrel; and cutting the heat set braided tube material to a desired length. The conforming step can be performed by at least partially wrapping tape over the braided tube material, or placing a shaping block having an internal opening complimentary to the mandrel, over the braided tube material.

A monofilament material having round or flat fibers may be used as the braided tube material. A sheet or strip of braid material may also be used in place of a tube, with the sheet or strip formed into a tube during the manufacturing process. For example, a strip of braid material may be wrapped around the mandrel and formed into a tube via the heat setting. A coating may be applied to at least part of the heat set braided tube.

Internal contact points of the braided tube material may optionally be embedded into the mandrel surface, and a coating applied onto at least part of the heat set braided material. One or both ends of the heat set braided material may be folded or rolled to form an atraumatic end.

FIGS. 9A and 9B show a finished access sheath 40, and demonstrate its ability to conform to significant angulation of surgical tools 42 and 44. The access sheath 40 can stretch as shown in FIG. 9B when surgical tools are angulated and apply a spreading load on the access sheath 40. In typical endonasal skull base procedures, multiple surgical tools are used to stretch the nares in order to increase the angle formed by two surgical tools creating a triangulation rather than bringing the distal ends of the surgical tools together. The access sheath 40 can preferably stretch as much as or more than the tissue of the nares. The access sheath 40 can accommodate the varied anatomy of the human nares and stretch and contract to accommodate surgical tool requirements.

The access sheath 40 may be compressed or folded for low profile placement and high profile working position. In a simple case the access sheath can be folded by hand and slid into the sinus manually. Loading tools or kits may also be used.

Figure 10A:
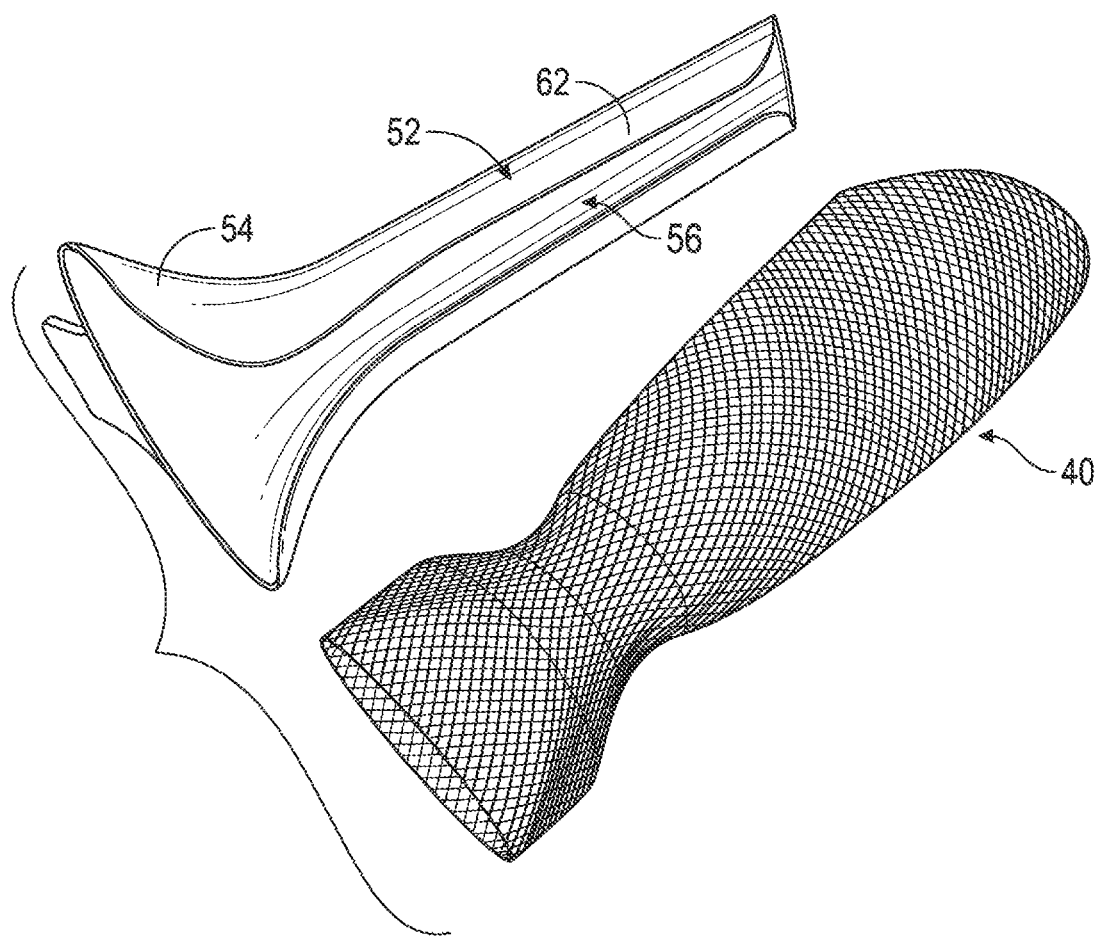
FIG. 10A shows the coated braided tube next two an introduction tool that has a longitudinal release slot.
Figure 10B:
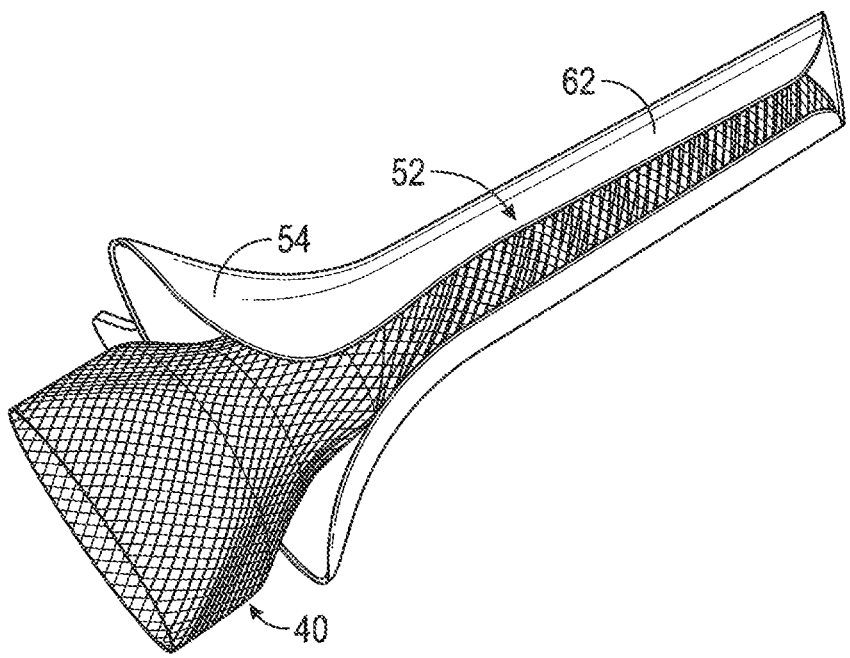
FIG. 10B shows the coated braided tube loaded into the introduction tool of FIG. 10A.
Figure 10C:
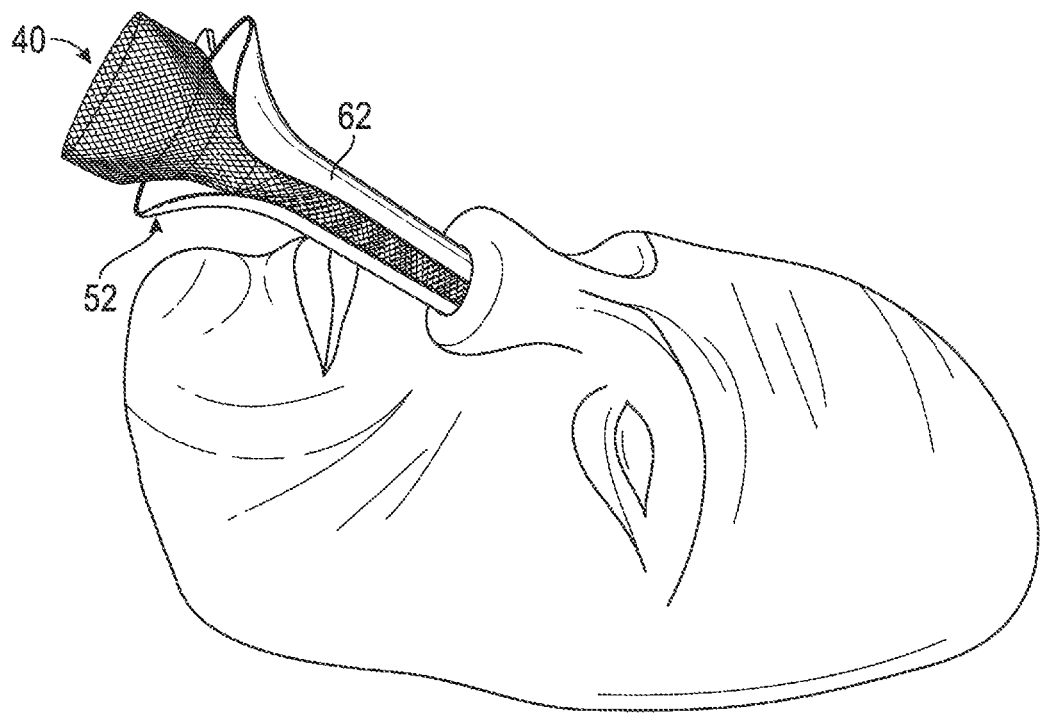
FIG. 10C shows the loaded introduction tool being inserted into the nose.
Figure 10D:
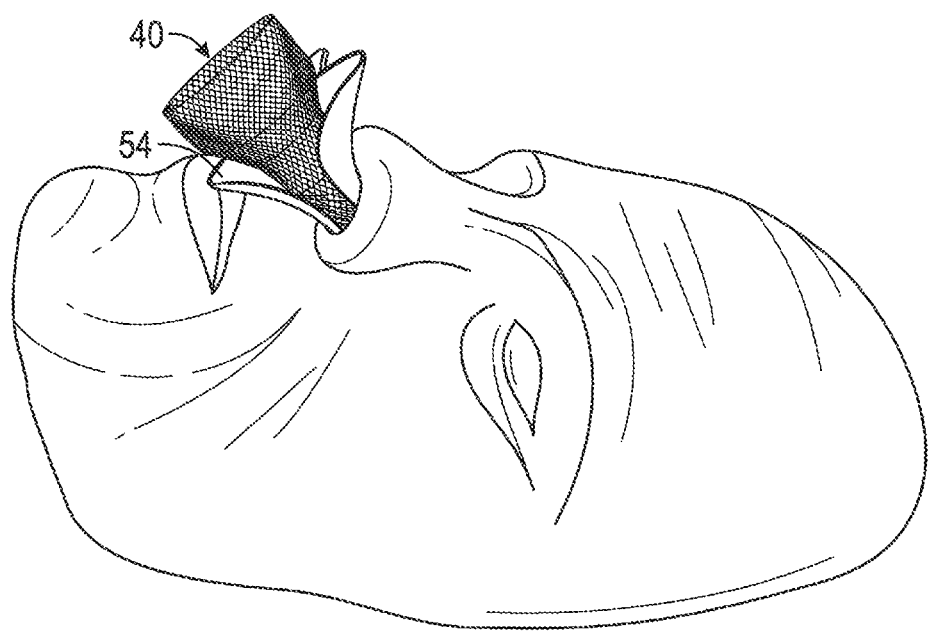
FIG. 10D shows the introduction tool fully inserted into the nose.
Figure 10E:
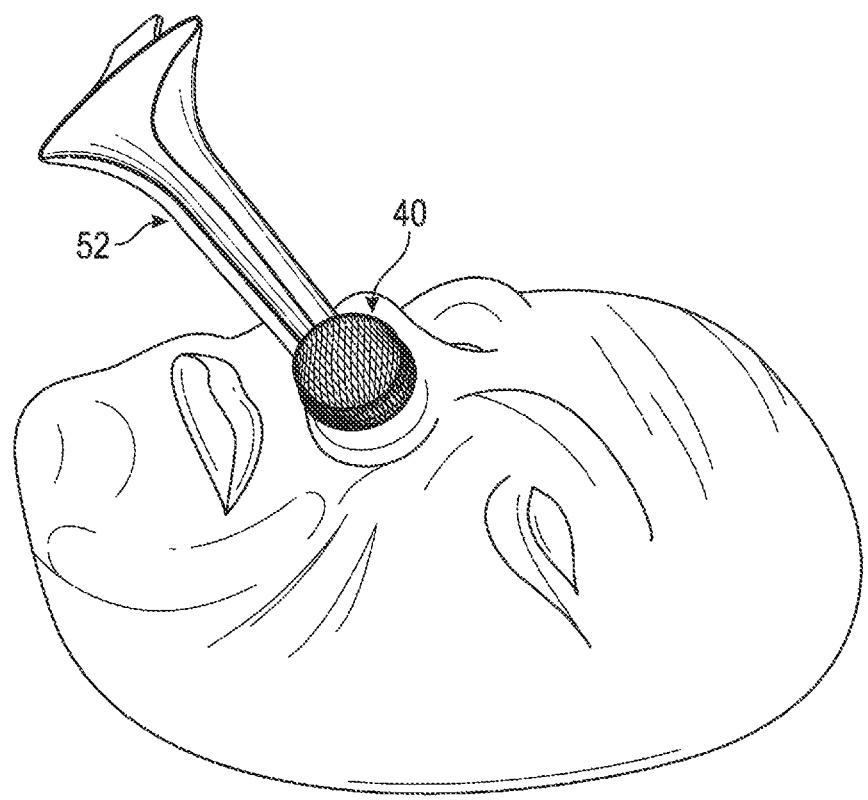
FIG. 10E shows the coated braided tube being mostly released out of the longitudinal release slot of the introduction tool.
Figure 10F:
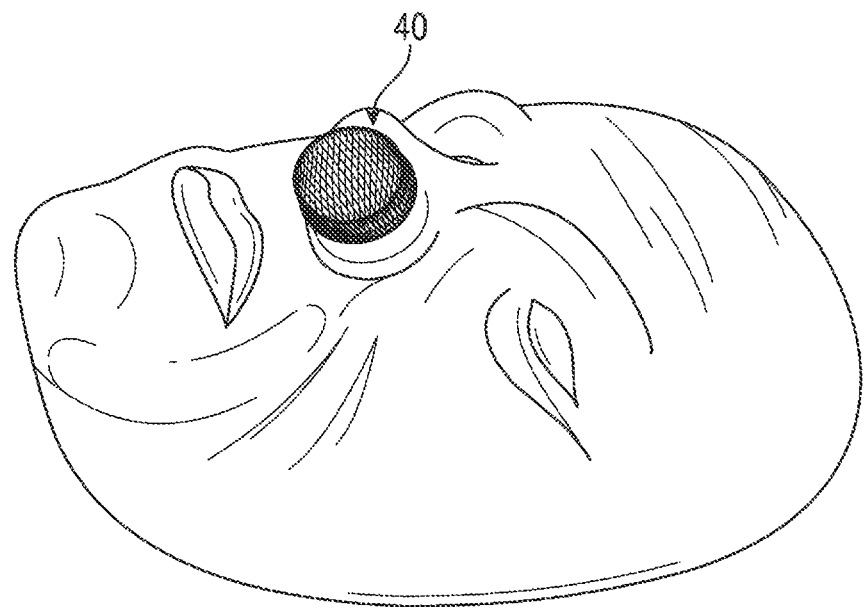
FIG. 10F shows the coated braided tube fully released out of the longitudinal release slot.

FIG. 10A-10F show a system or kit 50 for low-profile insertion of the access sheath 40. FIG. 10A shows the access sheath 40 next to an elongated tubular loading tool 52. The loading tool 52 has a flared proximal end 54 to aid in channeling the access sheath 40 into the elongated tubular body 62 of the loading tool 52. The loading tool 52 has an slot 56 along one side to allow the access sheath 40 to be separated from the loading tool after it is placed in the nose of the patient. FIG. 10B-10F show the placement of the access sheath 40. The access sheath 40 can be loaded via the loading tool 52 to 1) Compress and control the access sheath 40 into a compact volume; 2) provide a streamlined low profile shape for inserting the access sheath 40 into the narrow space of the nasal opening and cavity; and/or 3) provide a conduit for deploying the access sheath 40.

The loading tool 52 has a flared proximal end 54 to allow the access sheath 40 to be easily inserted into the loading tool 52 and compacted into a small volume. A tubular body 62 is joined to the flared proximal end 54 of the loading tool 52. The tubular body 62, which may be straight or have a slight taper towards the distal end, is designed to fit into the nasal opening. The slot 56 along the side of the loading tool 52 provides a conduit for the access sheath 40 to be deployed and released.

The kit in FIGS. 10A-10F may be provided with an access sheath 40 comprising a braid material, and a loading tool 52 having a conical proximal end, and a tubular distal end, and the slot 56 extending along one side of the loading tool, along the entire length of the loading tool. The loading tool comprises a flexible material to allow the slot to be pushed open further, to better allow the sheath to moved out of the loading tool into the nose or other body cavity. The slot has a width equal to 25% to 45% of a minimum diameter of the tubular distal end.

Figure 11A:
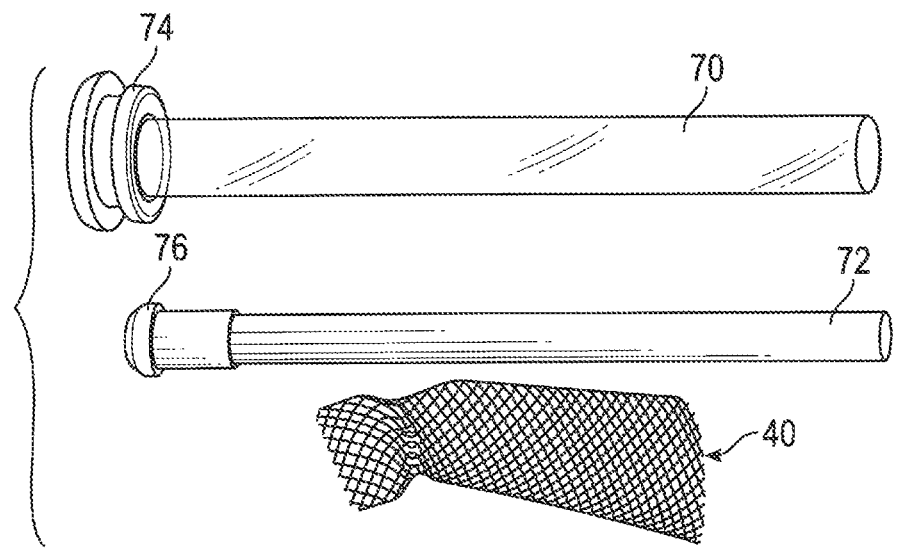
FIG. 11A shows the access sheath and a plunger deployment tool.
Figure 11B:
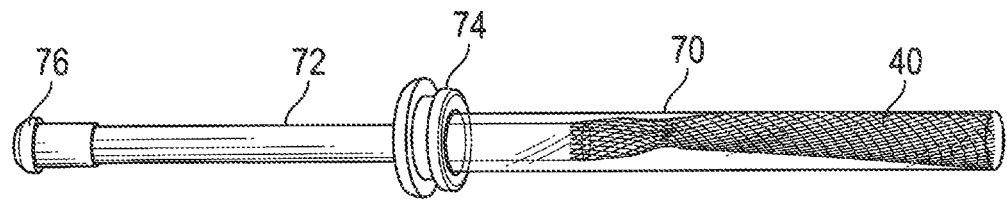
FIG. 11B shows the access sheath loaded in the plunger deployment tool.
Figure 11C:
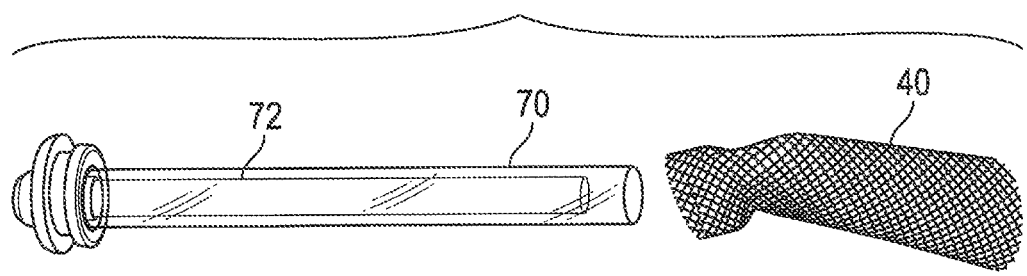
FIG. 11C shows the access sheath expelled distally from the plunger deployment tool.

Turning to FIG. 11A, in an alternative access sheath kit, the access sheath 40 may optionally be folded and slid into a tube 70. The tube 70 may be a thin walled round or oval tube, optionally with an annular collar 74 at the back or proximal end to provide a grasping surface. The folded or rolled access sheath 40 may be inserted into the distal or proximal end of the tube. The plunger 72 is inserted into the proximal end as shown in FIG. 11B. The tube 70 is then introduced into the nose. Advancing the plunger while holding the tube stationery pushes the access sheath 40 out of the distal end of the tube as shown in FIG. 11C. The tube and plunger may then be withdrawn by pulling back on the tube, leaving the access sheath 40 in place in the nose. The plunger 72 may have an enlarged head 76 having a diameter greater than the collar 74 or the tube 70, to limit the extent of travel of the plunger into the tube.

As shown in FIGS. 11A-11C, the surgical kit has an access sheath 40 made of a braided material, and a loading tool set including the tube 70 and the plunger 72 slidable into the tube. The access sheath 40 is foldable or compressible to fit into the tube, and with the access sheath expandable when ejected from the tube by the plunger. The tube may have an outside diameter of 5 to 20 mm and be transparent or translucent.

Figure 12A:
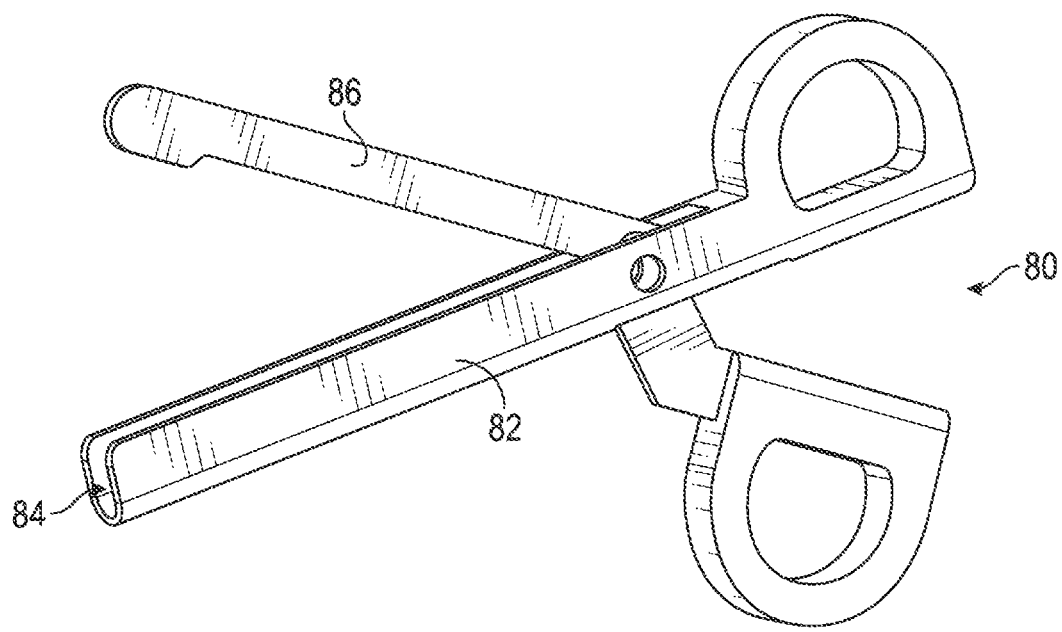
FIG. 12A shows a beam and groove scissor-like delivery tool in an open position.
Figure 12B:
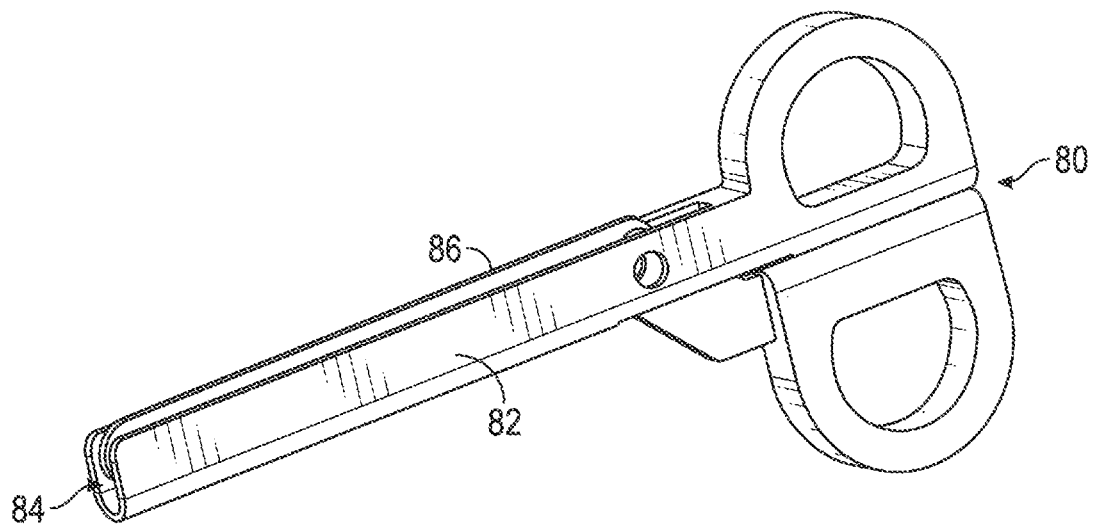
FIG. 12B shows the delivery tool of FIG. 12A in a closed position.
Figure 12C:
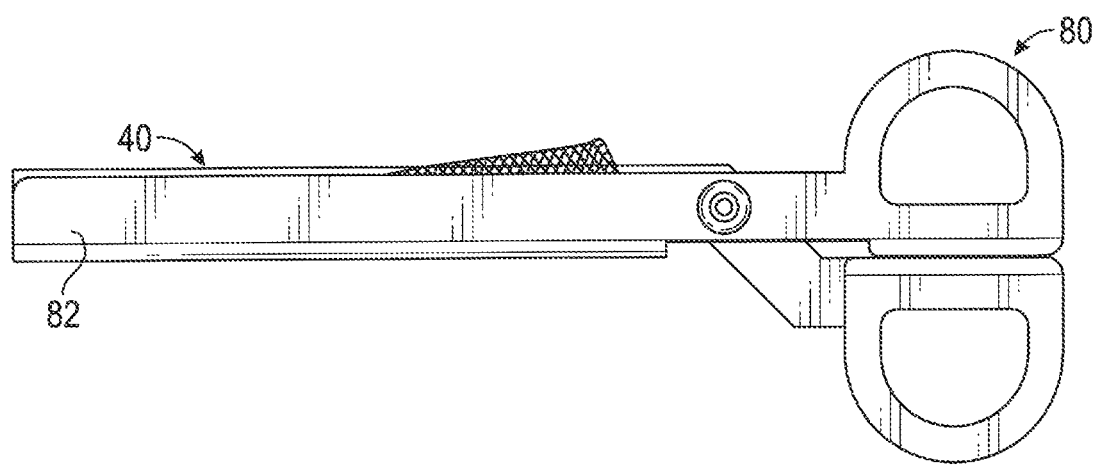
FIG. 12C is a top view of the access sheath of FIG. 5, 8A or 9 loaded onto the delivery tool.
Figure 12D:
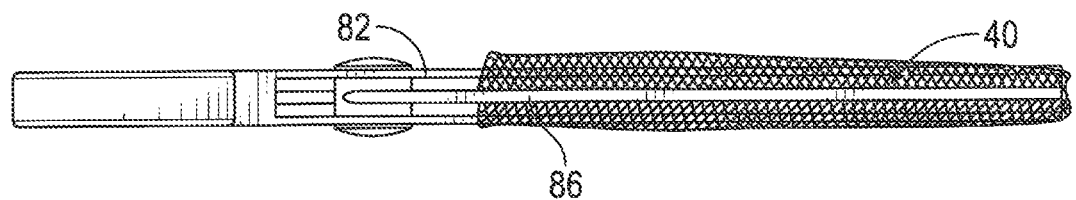
FIG. 12D is a side view of the access sheath and delivery tool shown in FIG. 12C.

FIG. 12A to 12C show another kit using a folding instrument 80 to fold, introduce and deploy the access sheath 40. The folding instrument 80 is a scissor-like device having a bottom jaw 82 having an elongated grooved channel 84. The top jaw 86 is an elongated rod or beam pivotally attached to the bottom jaw 82, with a handle at the back end of each jaw.

In use the instrument 80 is opened, as shown in FIG. 12A and the access sheath 40 is placed between the open jaws 82 and 86, or over one of the jaws. Squeezing the handles towards each other pivots the jaws towards a closed position shown in FIG. 12B, with the access sheath folded between the jaws. The jaws are then inserted into the nasal cavity and opened slightly to release the access sheath. The instrument 80 is removed while the access sheath 40 is left in place. The instrument 80 can be re-inserted into the internal channel 45 of the access sheath 40 and then manipulated open and closed to help open and expand the access sheath as needed.

The designs of FIGS. 12A-12C if provided as a surgical kit, includes the access sheath 40 made of a braid material, and the scissor-like loading tool having the first jaw pivotally attached to the second jaw, with the first jaw having a channel and the second jaw movable at least partially into the channel when the scissor-like loading tool is in a closed position, to fold the access sheath.

Figure 13A:
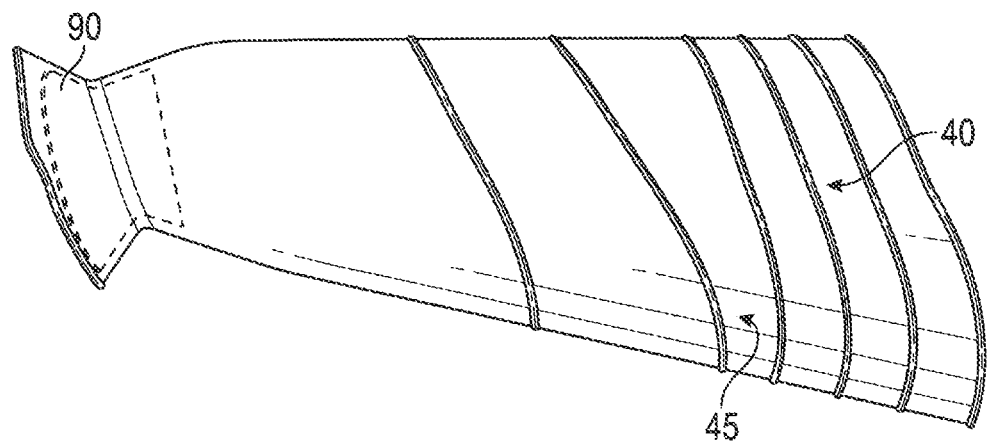
FIG. 13A is a side view of an embodiment of an elastomeric access sheath having a rigid plastic internal collar to create a low friction surface.
Figure 13B:
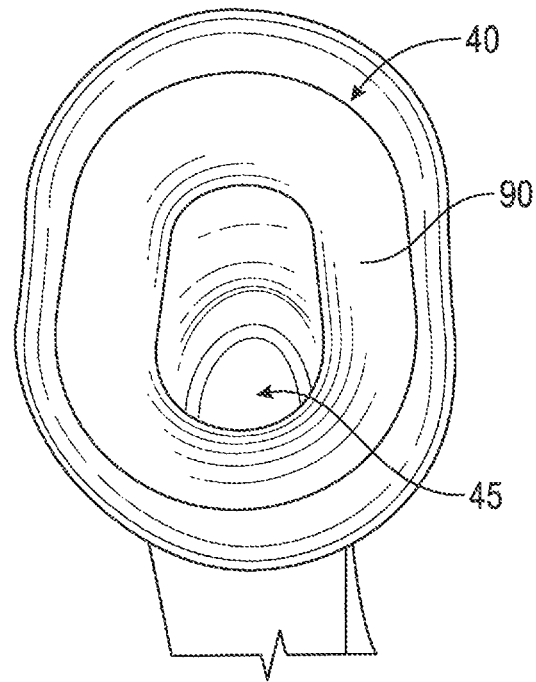
FIG. 13B is a front end view of the access sheath shown in FIG. 13A.
Figure 13C:
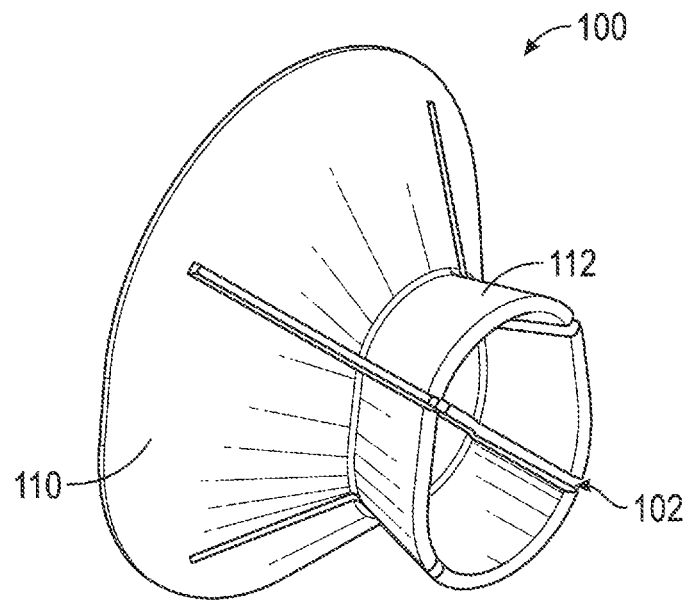
FIG. 13C shows a rigid collar for installment in an access sheath, with the rigid collar having radial slots to allow the rigid collar to flex.

Referring to FIGS. 13A and 13B, a conical collar insert 90 may be placed in the angle section 154 and flare section 156 of the access sheath 40, shown in FIGS. 15-22. The insert 90 may be made from a hard plastic or metal so that it is inherently lubricious relative to metal or plastic surgical tools 44. The insert 90 provides a lubricious bearing surface at the angle and flare sections of the access sheath 40, where surgical tools 44 extensively contact with the access sheath 40.

Figure 13D:
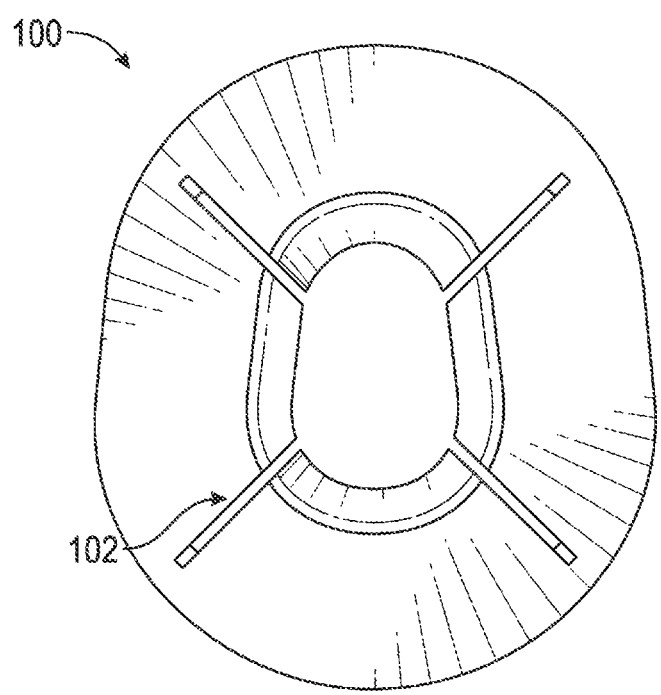
FIG. 13D shows the rigid collar of FIG. 13C installed in an access sheath.
Figure 13E:
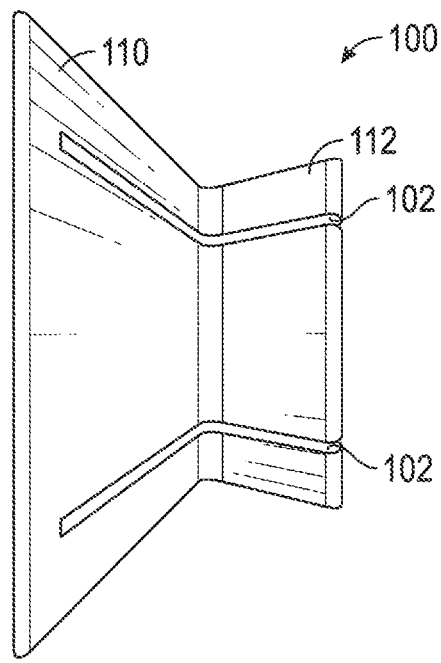
FIG. 13E is a side view of the rigid collar shown in FIG. 13C.
Figure 13F:
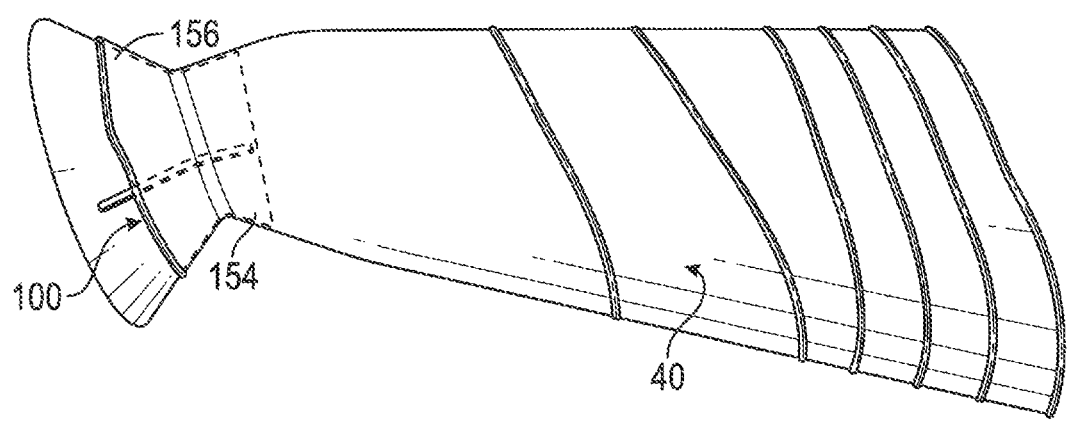
FIG. 13F is a side view of an embodiment of an elastomeric access sheath having the rigid plastic internal collar shown in FIG. 13C.

FIGS. 13B to 13E show an alternative conical collar insert 100 which is a rigid collar having radial slots 102 to allow it to flex into a more open state in response to forces exerted by surgical tools 44. This allows the surgical tools 44 to be more easily moved into larger acute angles relative to each other. The collar inserts 90 and 100 may each have a flared section 110 joined to a tubular section 112 having straight or parallel walls. Alternatively the tubular section 112 may have a reverse flare wherein it tapers outwardly towards the distal end. As shown in FIGS. 13A and 13D, the flared section 110 has a shape and dimensions to allow it to fit and be attached into the flare section 156 of the access sheath 40. The tubular section 112 is similarly configured to fit into the angle section 154 of the access sheath 40. The inserts 90 and 100 may be attached to the access sheath 40 via adhesive, plastics welding, shrink fit, molded into place, snap fit, etc.

Figure 14:
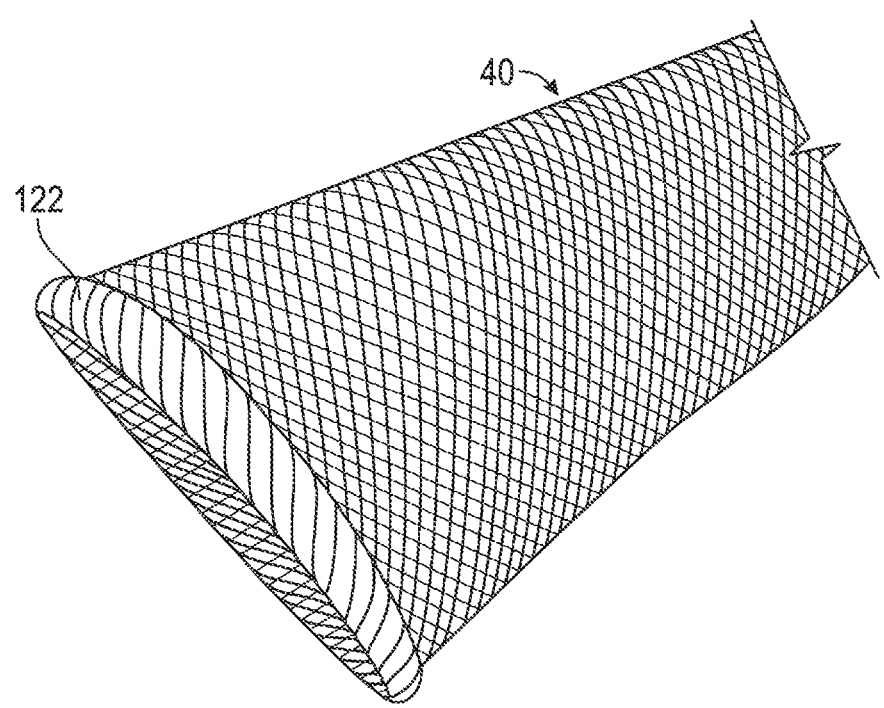
FIG. 14 shows the access sheath with an external rim of elastomer to create an atraumatic tip.

FIG. 14 shows an access sheath 40 with a distal end 120 of an elastomer to create an atraumatic tip 122. The elastomer can be an internal and external rim. Preferably the elastomer is only on the external surface so as not to create an internal surface of elastomer. This provides an atraumatic tip 122 but does not create an internal elastomeric surface that could result in a friction inducing surface at the distal end of the internal channel 45 of the access sheath 40. The elastomer may be provided a cut edge of a single layer of braided tube material, or over the rounded edge 32 of a access sheath 40 having two layers of braided tube material at the edge.

The elastomer may extend proximally 1-50 mm on the external surface of the access sheath 40. The external extended elastomeric surface 124 provides a user selectable section that may be cut to a desired length. When cut, a portion of the external extended elastomeric surface 124 remains on the access sheath 40 and provides an atraumatic distal rim. An external rim of elastomer may similarly be used on the proximal end of the access sheath. This provides a section at the proximal end that maintains the integrity of the braided tube and avoid fraying. The external rim of elastomer on the proximal rim, if used, may only be on the external surface so as not to create friction on surgical tools passing through the internal channel 45.

Figure 16:
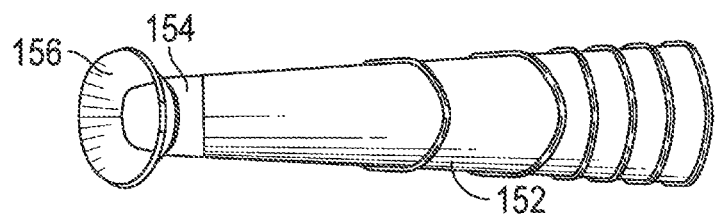
FIG. 16 is a bottom view of the sheath shown in FIG. 15.
Figure 17:
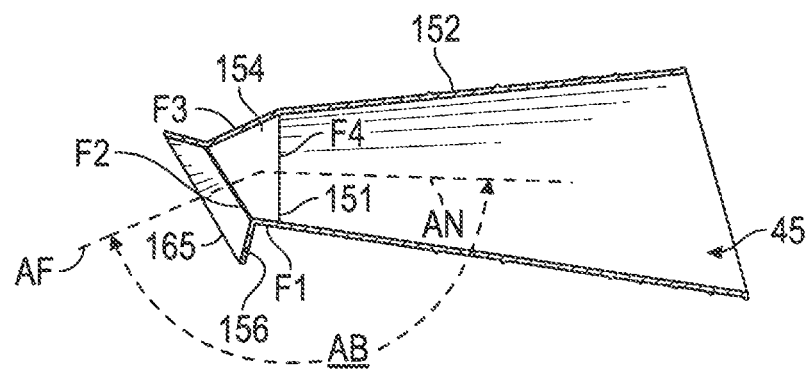
FIG. 17 is a section view of the sheath shown in FIG. 15.
Figure 18:
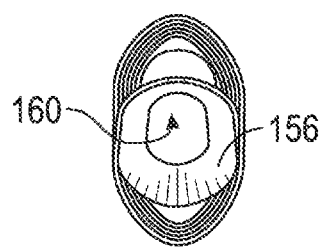
FIG. 18 is left end view of the sheath of FIG. 15.
Figure 19:
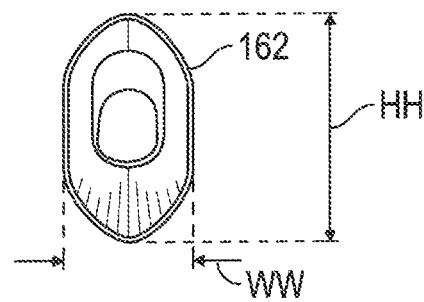
FIG. 19 is a right end view of the sheath of FIG. 15.
Figure 20:
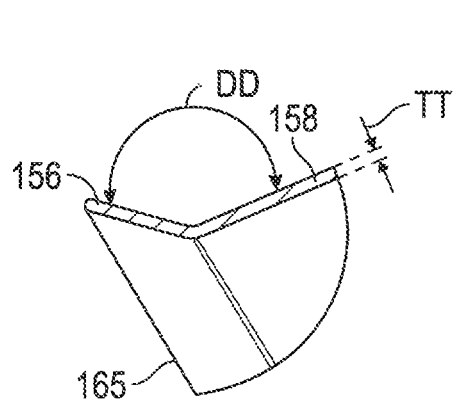
FIG. 20 is an enlarged detail view of detail A shown in FIG. 18.
Figure 21:
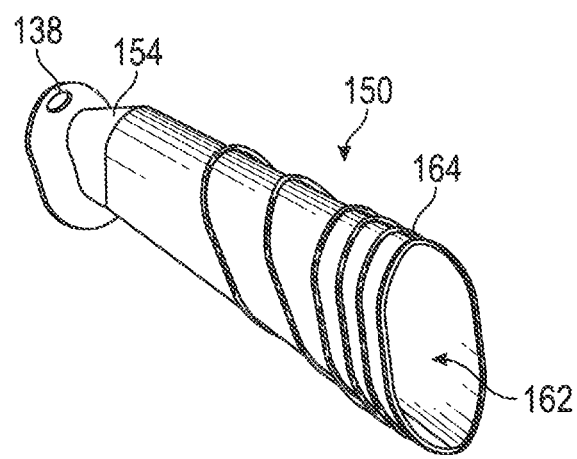
FIG. 21 is front, top and right side perspective view of the sheath shown in FIG. 15.
Figure 22:
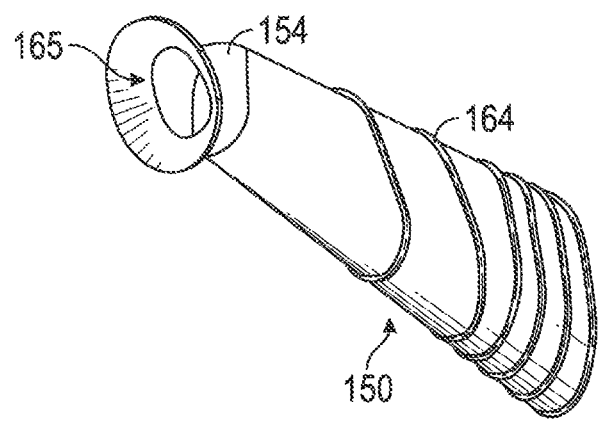
FIG. 22 is rear, bottom and right side perspective view of the sheath shown in FIG. 15

FIGS. 15-22 show dimensions and angles which may be used for the access sheath 40. The mandrel 22 may be sized and shaped to form an access sheath as shown in these Figures. In this example, the access sheath 40 has a body section 152, and angle section 154 and a flare or conical section 156. The sheath 40 may be formed of braid material as a one piece unit with the body section 152, the angle section 154 and the flare section 156 integrally joined together. As shown in FIG. 20, the sheath 40 may have a thin flexible wall 158 having a thickness TT which allows the sheath to conform to the body orifice, or the inner wall of the patient's nostrils in the case of nasal access. The flare section 156 may be provided as a conical ring forming an angle DD of 120-160 or 130-150 degrees with the top wall of the angle section. The sheath 40 may have a single through internal channel 45 extending from a distal opening 162 to a proximal opening 165. As shown in FIGS. 18, 19 and 22, the openings 162 and 165, and the cross section of the body section 152, may be generally in the shape of an oval or an ellipse.

Figure 15:
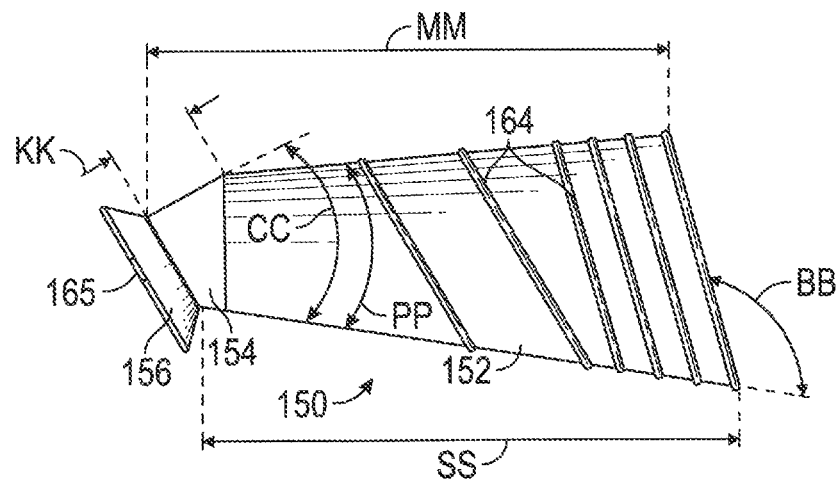
FIG. 15 is a side view of the access sheath of FIGS. 3-9B with preferred dimensions and angles.

Referring to FIGS. 15 and 17, the distal opening 162 may lie in a plane forming an angle forming an angle BB with the bottom of the sheath 40, with BB ranging from 95 to 125 or 100 to 115 degrees. As best shown in FIG. 17, the angle section 154 may be described as joined to the body section 152 at a vertical line 151. The upper and lower walls of the sheath extend distally away from the vertical line 151 towards the distal opening 162 at acute angles to the vertical line 151, which may the same or different angles. As shown in FIG. 15, the included angle CC between the top surface of the angle section 154 and the lower wall of the body section may range from 25 to 40 or 30 to 35 degrees. The angle PP in FIG. 15 relating to the diverging angle of the top and bottom surfaces of the body section is typically 10-20 or 12-16 degrees. Dimension KK may be 8-16 or 10-14 mm, with dimensions MM and SS both generally about 65-85 or 70-80 mm.

As shown in FIGS. 15-17, a surgical sheath 40 includes a conical section; an angle section joined to the conical section, with the conical section having a central axis AF not parallel to a central axis AN of the angle section; a body section joined to the angle section, with the body section having a length at least twice the length of the angle section; and the conical section, the angle section and the body section comprising a braid material. The sheath 40 may further include an insert 90, 100 inside of the conical section, with the insert made of a non-braid material. An elastomer coating may be provided on at least part of an external surface of the sheath. The sheath may have a rolled edge at its distal end.

Turning to FIGS. 15-16 and 20-22, one or more ridges 64 may be provided on an outer surface of the body section 152. The ridges may optionally be provided as rings extending continuously around the outside surface of the body section. The dimensions and angles shown in the drawings of all embodiments may typically be varied by 10, 20 or 30% depending on various design parameters.

The angle section 154 may allow the proximal end of the sheath 40 to be more easily stretched and/or deflected. This allows for more versatile movement of surgical tools extending through the sheath during surgery. As shown in FIGS. 15 and 17 the angle section 154 forms an irregular quadrilateral shape in cross section. In FIG. 17 the angle section 154 may be defined by line F4 along with segments or lines F1, F2 and F3, with F4 and F2 forming a first acute angle and with F1 and F3 forming a second acute angle. Each of the sides or segments F4, F1, F2 and F3 forming the angle section 154 may also have different lengths. F3 may be substantially perpendicular to F2. The angle section 154 may alternatively be described via a centerline AN perpendicular to and bisecting segment or line F4 and intersecting a centerline AF of the flare section 156 at an angle AB of 5-30 or 10-20 degrees.

One method for placing a surgical access sheath includes loading a surgical access sheath into a loading tool, with the surgical access sheath comprising a braid material, and with the loading tool having a conical proximal end, and a tubular distal end, and a slot extending from the conical proximal end to the tubular distal end; inserting the loading tool into a body orifice; inserting a surgical tool into an internal channel of the surgical access sheath; moving the surgical tool to move the surgical access sheath out of the loading tool through the slot; and withdrawing the loading tool from the body orifice.

Another method for placing a surgical access sheath includes placing a surgical access sheath into a low profile delivery position, with the surgical access sheath comprising a braid material; loading the surgical access sheath into a tube; inserting the loading tool into a body orifice; moving a plunger into the tube to eject the surgical access sheath out of the tube and into the body orifice; and withdrawing the tube from the body orifice.

Another method for placing a surgical access sheath includes providing a scissor-like loading tool having a first jaw pivotally attached to a second jaw, with the first jaw having a channel and the second jaw movable at least partially into the channel when the scissor-like loading tool is in a closed position; providing a surgical access sheath comprising a braid material, with the access sheath having an internal channel; placing the access sheath around one of the first jaw and the second jaw, while the jaws are in an open position; moving the jaws into the closed position, to fold and grasp the surgical access sheath; inserting the jaws into a body orifice; opening the jaws to release the surgical access sheath; and removing the jaws from the body orifice.

A surgical kit includes an access sheath comprising a braid material; and a loading tool having a conical proximal end, and a tubular distal end, and a slot extending from the conical proximal end to the tubular distal end. The loading tool may comprise a flexible material. Typically the slot extends along an entire length of the loading tool. The slot may have a width equal to 25% to 45% of a minimum diameter of the tubular distal end. The access sheath may have a conical section, an angle section joined to the conical section, with the conical section having a central axis AF not parallel to a central axis AN of the angle section, a body section joined to the angle section, with the body section having a length at least twice the length of the angle section. Alternatively, the loading tool may have a tube and a plunger slidable into the tube, with the access sheath foldable or compressible to fit into the tube, and with the access sheath expandable when ejected from the tube by the plunger. If used, the tube may have an outside diameter of 5 to 20 mm, and it may be transparent or translucent. A scissor-like loading tool may also be used, with the scissor-like loading tool having a first jaw pivotally attached to a second jaw, with the first jaw having a channel and the second jaw movable at least partially into the channel when the scissor-like loading tool is in a closed position, to fold the access sheath.

Thus, a novel surgical sheath and methods have been shown and described. Various changes and substitutions may of course be made without departing from the spirit and scope of the invention. The invention, therefore, should not be limited except by the following claims and their equivalents.

The invention claimed is:

1. A surgical method comprising:
grasping an outside surface of a first end of a flexible sheath between first and second jaws of a sheath placement instrument by pivoting the first jaw towards the second jaw, the flexible sheath having a conical section, an angle section and a body section;
pulling the first end of the flexible sheath into a nasal cavity of a patient using the sheath placement instrument;
inserting a distal end of a first surgical tool entirely through the flexible sheath to position the distal end of the first surgical tool at an operating site;
inserting a distal end of a second surgical tool entirely through the flexible sheath to position the distal end of the second surgical tool at the operating site;
using the first surgical tool and the second surgical tool to perform a surgical procedure at the operating site;

withdrawing the first surgical tool and the second surgical tool from the flexible sheath; and removing the flexible sheath from the nasal cavity.

2. The method of claim 1 further comprising stretching or deflecting the conical section by angulating the first surgical tool relative to the second surgical tool.

3. The method of claim 1 wherein the conical section is a right conical section, further including moving a proximal end of the first surgical tool relative to the second surgical tool to stretch or deflect the conical section.

4. The method of claim 3 further including stretching tissue of the nares.

5. The method of claim 3 wherein the flexible sheath comprises a braided material made of hard plastic fibers and the flexible sheath has a non-continuous undulating interior surface.

6. The method of claim 5 wherein the first surgical tool contacts discrete contact points on the non-continuous undulating surface.

7. The method of claim 3 wherein the flexible sheath comprises a braided material tube, and the conical section adjoins the angle section along a line F2 which is parallel to a plane of a proximal opening of the conical section.

8. The method of claim 7 with a distal end of the conical section joined to a proximal end of the angle section, with the conical section having a central axis AF not parallel to a central axis AN of the angle section, and the body section is joined to a distal end of the angle section, with the body section having a length at least twice the length of the angle section, and wherein the sheath has an impermeable coating.

9. The method of claim 7 wherein a centerline of the body section does not intersect any part of the flexible sheath, before the sheath is placed in the nasal cavity.

10. The method of claim 1 further including moving the surgical sheath to a position where the conical section is entirely outside of the nasal cavity and the body section is entirely inside of the nasal cavity.

11. The method of claim 1 further including viewing the surgical site using at least one of the first and second surgical tools.

12. The method of claim 1 further including creating a fold in the flexible sheath before placing it into the nasal cavity.

13. The method of claim 1 wherein the flexible sheath comprises an is impermeable coated braided material.

14. A method of using a surgical sheath, comprising:
providing a surgical sheath having a conical section, an angle section and a body section, the sheath made of a braided material;
moving the surgical sheath to a position where the conical section is entirely outside of a nasal cavity and the angle section and the body section are entirely inside of the nasal cavity;
inserting a distal end of a first surgical tool entirely through the sheath to position the distal end of the first surgical tool at an operating site;
inserting a distal end of a second surgical tool entirely through the sheath to position the distal end of the second surgical tool at the operating site;
performing a surgical procedure using the first and second surgical tools;
withdrawing the first surgical tool and the second surgical tool from the sheath; and
removing the sheath from the nasal cavity.

15. The method of claim 14 further comprising grasping an outside surface of the body section of the sheath between first and second jaws of a sheath placement instrument and using the sheath placement instrument to pull the sheath into the nasal cavity.

16. The method of claim 14 further including using the first surgical tool and the second surgical tool to stretch or deflect the conical section by angulating the first surgical tool relative to the second surgical tool.

17. A method of using a surgical sheath, comprising:
providing a surgical sheath having a conical section, an angle section and a body section, the sheath made of a braided material;
moving the surgical sheath into a nasal cavity;
inserting a distal end of a first surgical tool entirely through the sheath to position the distal end of the first surgical tool at an operating site;
inserting a distal end of a second surgical tool entirely through the sheath to position the distal end of the second surgical tool at the operating site;
using the first surgical tool and the second surgical tool to stretch or deflect the conical section by angulating the first surgical tool relative to the second surgical tool;
removing the first and second surgical tools; and
removing the sheath from the nasal cavity.

18. The method of claim 17 further comprising grasping an outer surface of the body section of the sheath between first and second jaws of a sheath placement instrument and using the sheath placement instrument to pull the sheath into the nasal cavity.

19. The method of claim 18 further including moving the surgical sheath to a position where the conical section is entirely outside of a nasal cavity and the angle section and the body section are entirely inside of the nasal cavity.

20. The method of claim 19 wherein the sheath is made of an impermeable coated braid of hard plastic fibers, the conical section is a right conical section adjoining the angle section along a line which is parallel to a plane of a proximal opening of the right conical section, a centerline of the body section not intersecting any part of the sheath, the sheath having a non-continuous undulating interior surface; further including creating a fold at a first end of the body section, and grasping the fold between first and second jaws of the sheath placement instrument.

* * * * *